United States Patent [19]
Golosarsky et al.

[11] Patent Number: 5,718,235
[45] Date of Patent: Feb. 17, 1998

[54] DETECTION OF ABNORMAL AND INDUCTION OF NORMAL HEART RATE VARIABILITY

[75] Inventors: Boris Golosarsky, Cincinnati, Ohio; Nicholas Wood, Rowayton, Conn.

[73] Assignee: GW Scientific, Inc., Rowayton, Conn.

[21] Appl. No.: 689,144

[22] Filed: Jul. 30, 1996

Related U.S. Application Data

[63] Continuation of Ser. No. 482,980, Jun. 7, 1995, abandoned, which is a continuation-in-part of Ser. No. 274,321, Jul. 13, 1994, abandoned, which is a continuation of Ser. No. 957,611, Oct. 6, 1992, abandoned.

[51] Int. Cl.$^6$ .................................................. A61B 5/0456
[52] U.S. Cl. .................................. 128/708; 128/697
[58] Field of Search .................................. 128/696, 697, 128/702, 704, 705, 708, 903, 904; 607/14, 17, 27

[56] References Cited

U.S. PATENT DOCUMENTS

| | | |
|---|---|---|
| D. 278,746 | 5/1985 | Saynajakangas . |
| D. 287,403 | 12/1986 | Kiiski et al. . |
| 4,312,356 | 1/1982 | Sowton et al. . |
| 4,453,537 | 6/1984 | Spitzer . |
| 4,531,527 | 7/1985 | Reinhold, Jr. et al. . |
| 4,572,192 | 2/1986 | Jackman et al. . |
| 4,625,733 | 12/1986 | Säynäjäkangas . |
| 4,883,063 | 11/1989 | Bernard et al. . |
| 4,960,129 | 10/1990 | dePaola et al. . |
| 5,042,497 | 8/1991 | Shapland . |
| 5,058,597 | 10/1991 | Onoda et al. . |
| 5,078,133 | 1/1992 | Heinz et al. . |
| 5,437,285 | 8/1995 | Verrier et al. . |
| 5,462,060 | 10/1995 | Jacobson et al. . |
| 5,522,854 | 6/1996 | Ideker et al. . |
| 5,560,370 | 10/1996 | Verrier et al. . |

FOREIGN PATENT DOCUMENTS

| | | |
|---|---|---|
| 1607808A1 | 11/1990 | U.S.S.R. . |
| 1683679A1 | 10/1991 | U.S.S.R. . |
| 1769894A1 | 10/1992 | U.S.S.R. . |

OTHER PUBLICATIONS

"The Functional Model Regulation Homeokinesis of Heart Rhythm;"Golosarsky B., research worker, Odessa Research Institute of Medical Rehabilitation (1989).

(List continued on next page.)

*Primary Examiner*—George Manuel
*Attorney, Agent, or Firm*—Watson Cole Stevens Davis, P.L.L.C.

[57] ABSTRACT

The duration of Time Intervals, preferably 101, in an electrocardiogram, or pulses are recorded. The Mode, [Mo], or the duration most often recorded, the Median, [M], of all durations recorded, the Amplitude of the Mode, [AMo], expressed as a percentage of the most frequently recorded Modes, and the difference in duration between the longest and the shortest duration recorded, Delta X, [DX], are determined and consolidated into one or more Cluster Modes, [CMo], comprised of three Modes each, establishes a user's baseline. If any of the 9 formulas derived from these functions differs by a predetermined percentage and time duration from the user's baseline, then the user's stress has reached an ALARM level. The apparatus make take the form of a chest strap on which are mounted electrocardiogram electrodes, which transmits Time Intervals to a wrist watch like device where the calculations are performed and the results displayed. If an ALARM is detected, the cellular telephone component is activated to transmit the user's distressed state to a care provider. The apparatus may also take the form of a wrist mounted pulse transducer in lieu of the chest mounted electrodes. The apparatus may also take the form of a cardioverter defibrillator or pacemaker. If an over stressed state is detected, activate natural pacing of the user's heart by using either the user's own prerecorded natural heart rhythm variability or the natural heart rhythm variability of an individual matched to the user as to age, sex and physical condition.

66 Claims, 28 Drawing Sheets

OTHER PUBLICATIONS

Malik, Farrell, Cripps, Camm, Heart Rate Variability in Relation to Prognosis After Myocardial Infarction: Selection of Optimal Processing Techniques. *Eur. Heart J.* 1989;10:1060–1074.

Malik, Xia, Odemuyiwa, Staunton, Poloniecki, Camm, Influence of the Recognition Artefact in the Automatic Analysis of Long–term Electrocardiograms on Time–domain Measurement of Heart Rate Variability, *Med. Biol. Eng. Comput.* 1993;31:539–544.

Malik, Camm, Components of Heart Rate Variability: What They Really Mean and What We Really Measure, *Am. J. Cardiol.* 1993; 72:821–822.

Malik, Cripps, Farrell, Camm., Prognostic Value of Heart Rate Variability After Myocardial Infarction: A Comparison of Different Data Processing Methods, *Med. Biol. Eng. Comput.* 1989;27:603–611.

Malik, Camm, Heart Rate Variability and Clinical Cardiology, *Br. Heart J.* 1994; 71:3–6.

Malik, Camm. Significance of Long–term Components of Heart Rate Variability for the Further Prognosis After Acute Myocardial Infarction, *Cardiovasc. Res.* 1990;24:793–803.

Fei, Malik, Short–and Long–term Assessment of Heart Rate Variability for Postinfarction Risk Stratification, In: Malik, Camm, eds, *Heart Rate Variability*, Armonk, NY: Futura; 1995: 341–346.

Heart Rate Variability Standards of Measurement, Physiological Interpretation, and Claincal Use, Circulation, vol. 93, No. 5 (Mar. 1, 1996).

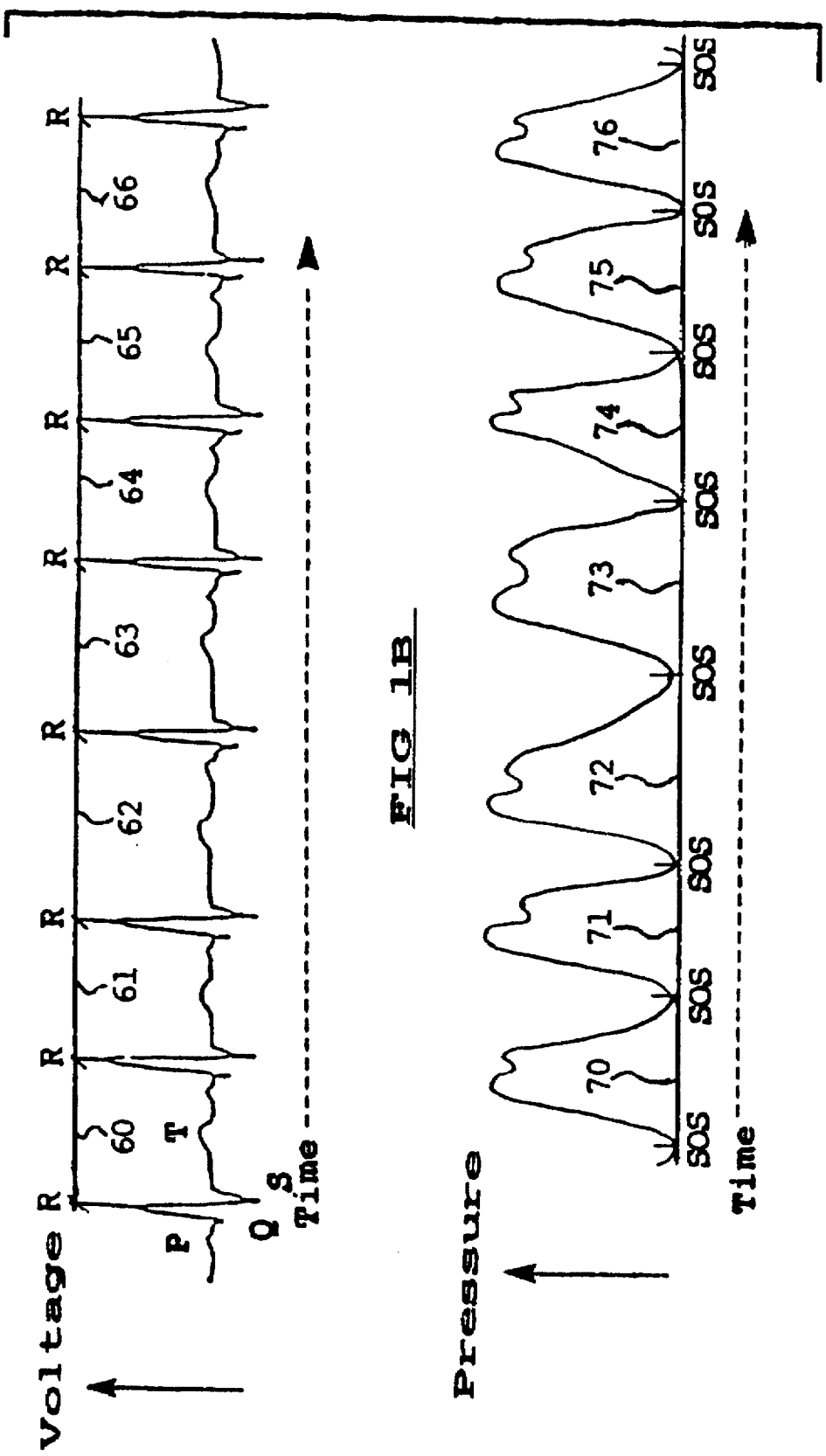

| FIG 4A |
| FIG 4B |
| FIG 4C |

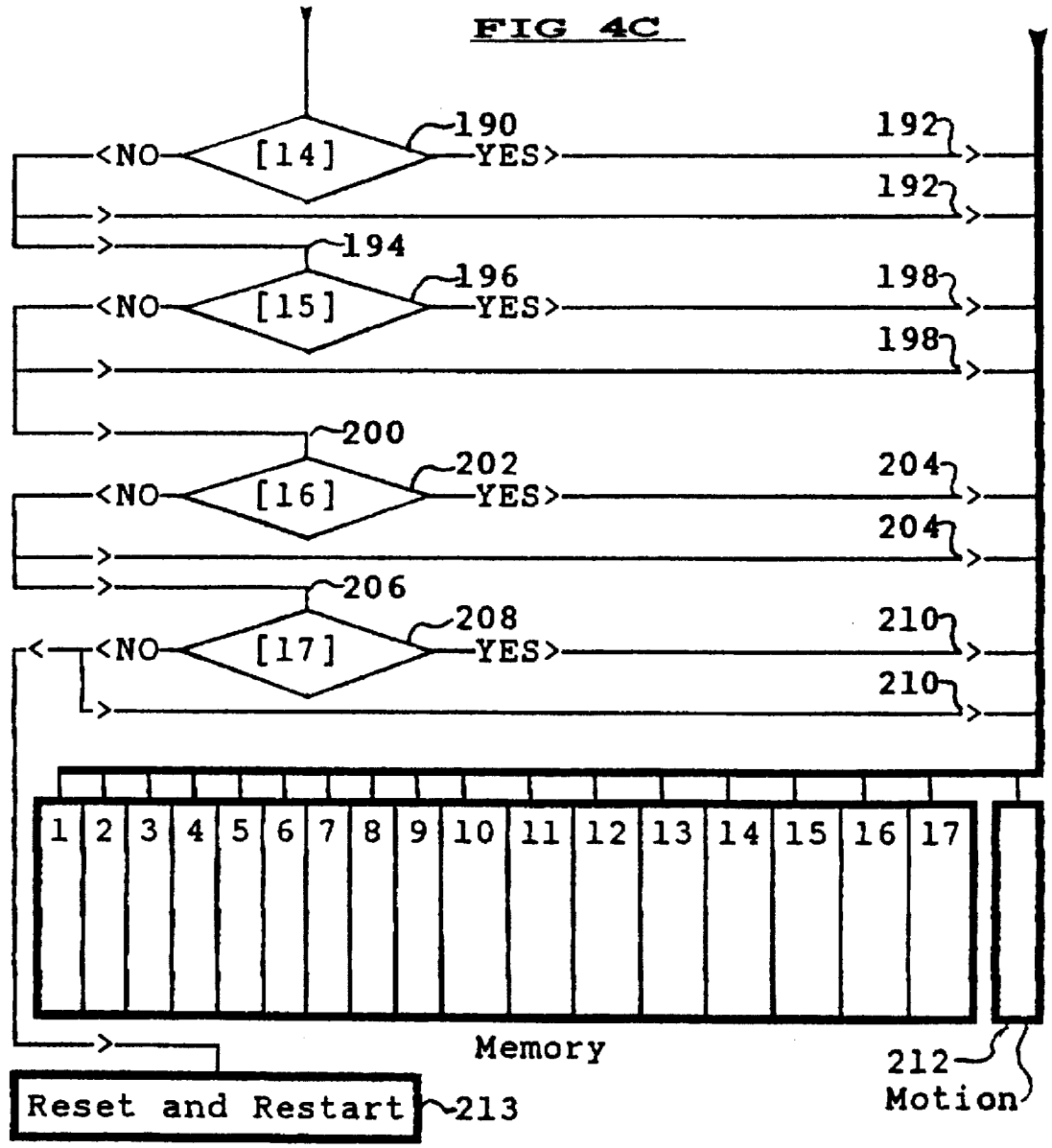

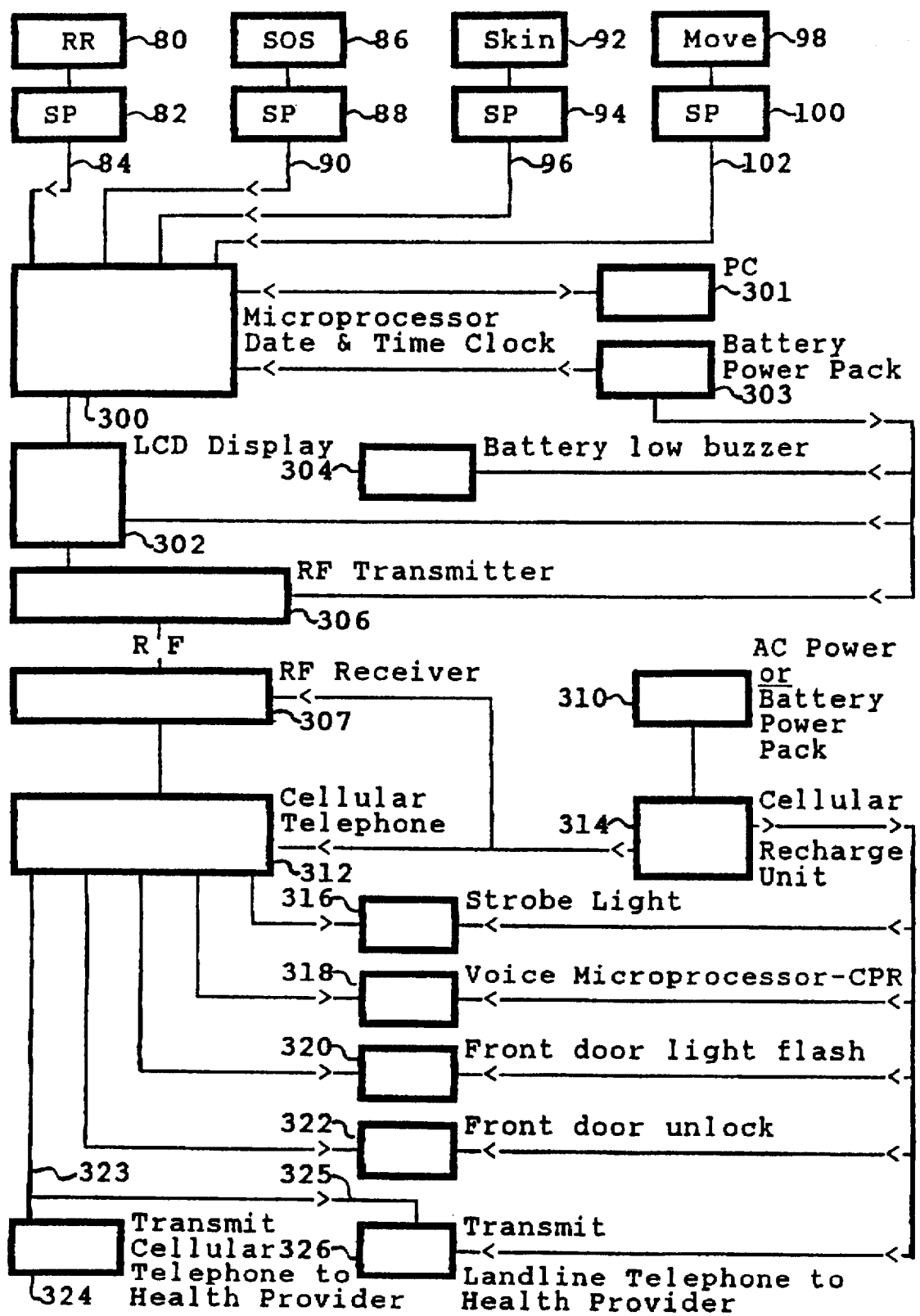

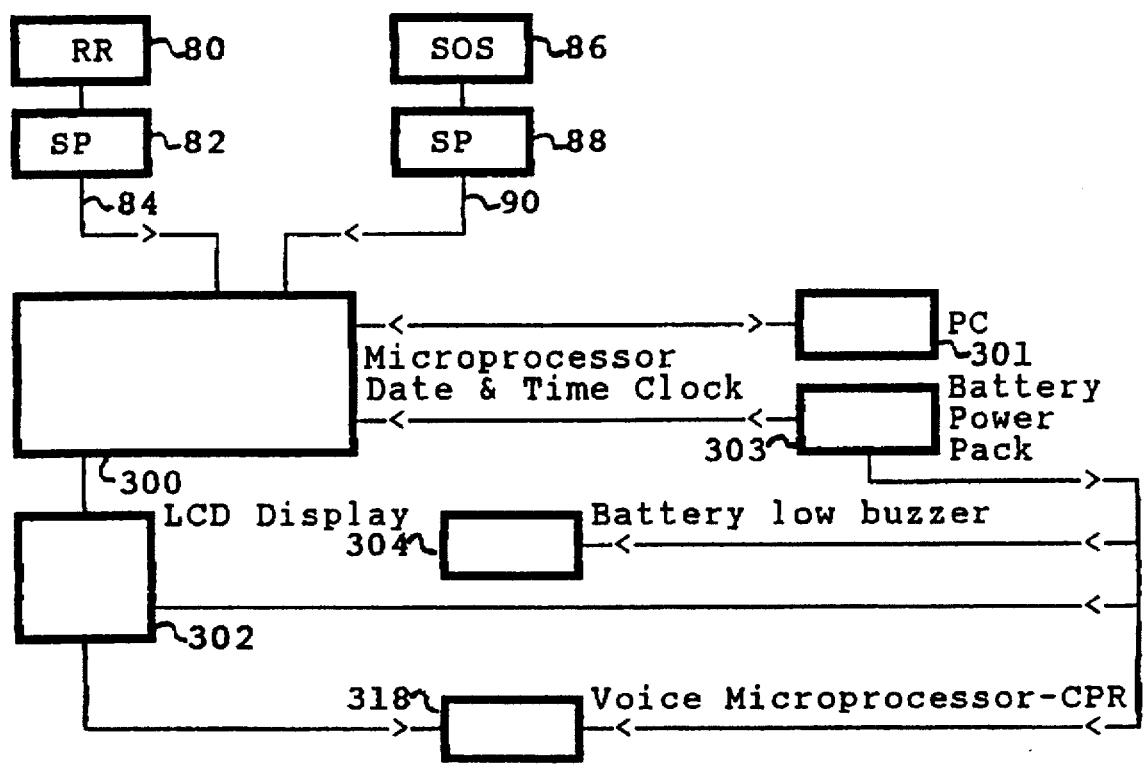

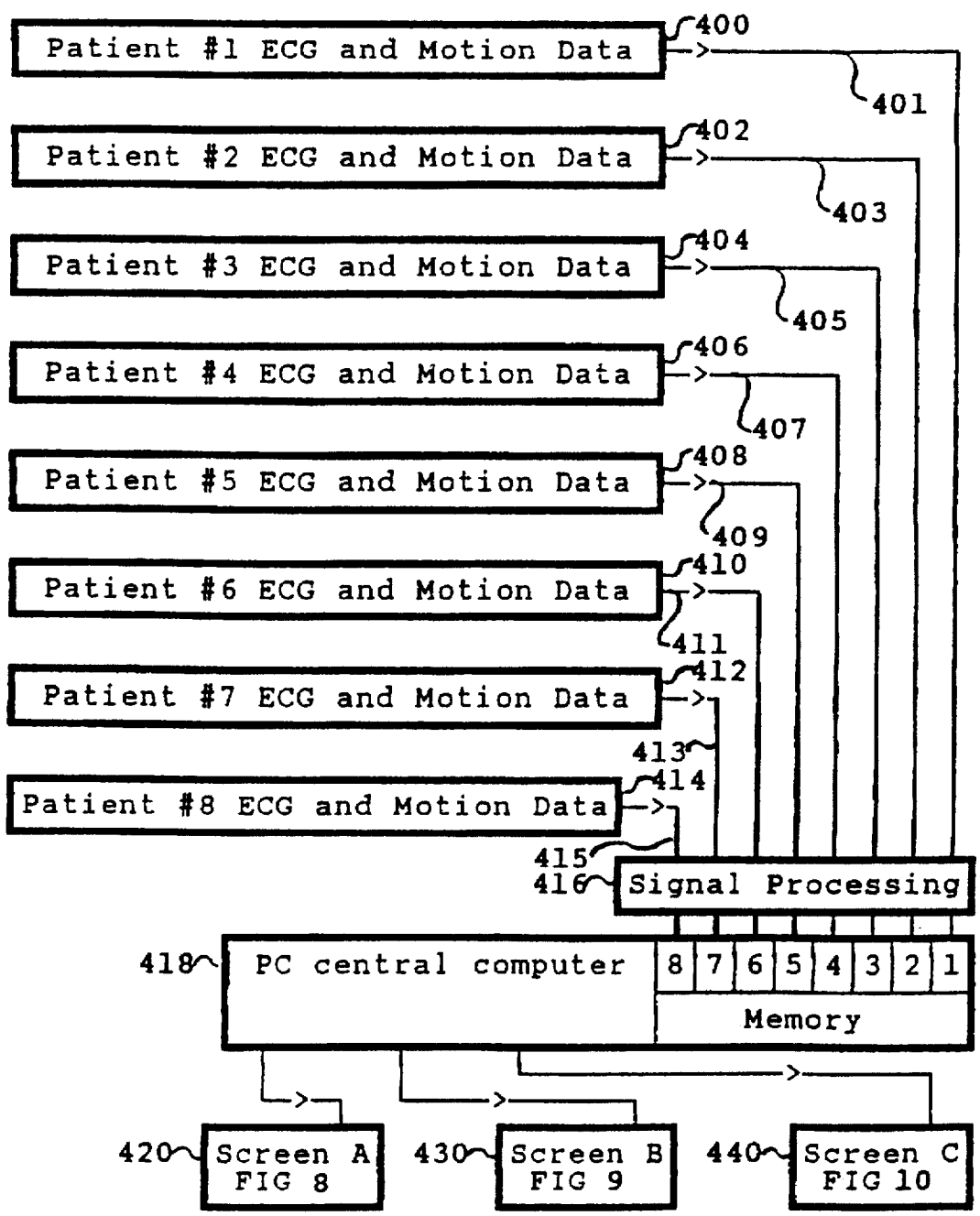

FIG 8

| Patient | Room | UV | AMo | DX | PVC | BPM | Status UV | AMo | DX | ALARM Set | ALARM Duration |
|---|---|---|---|---|---|---|---|---|---|---|---|
| Patient 1 | 812A | 6.7 | 35 | .12 | 0 | 78 | OK | OK | OK | 30 | 0 |
| Patient 2 | 805B | 13.1 | 45 | .08 | 1 | 85 | S | S | OK | 30 | 6 |
| Patient 3 | 810A | 13.5 | 44 | .08 | 5 | 88 | P | OK | P | 30 | 3 |
| Patient 4 | 801B | 7.2 | 42 | .10 | 0 | 81 | OK | OK | OK | 30 | 0 |
| Patient 5 | 814A | 7.5 | 36 | .12 | 0 | 75 | OK | OK | OK | 30 | 0 |
| Patient 6 | 809B | 8.5 | 37 | .12 | 0 | 72 | OK | OK | OK | 30 | 0 |
| Patient 7 | 802B | 3.2 | 21 | .18 | 0 | 96 | OK | P | OK | 30 | 27 |
| Patient 8 | 802A | 40.1 | 80 | .06 | 7 | 102 | S | S | S | 30 | 31 |

Date: 12/01/94    Time: 18:02    GWS

FIG 9

| Patient | Room | UV | AMo | DX | PVC | BPM | ALARM Set | ALARM Duration |
|---|---|---|---|---|---|---|---|---|
| Patient 8 | 802A | S40.1 | S80 | S.06 | 7 | 102 | 30 | 31 |
| ALARM Settings | | S42.3 | S81 | S.06 | 8 | 101 | " | 29 |
| Base — MF — ALARM | | | | | | | | |
| SUV  1.2   22.8 | | S43.2 | S80 | S.06 | 9 | 97 | " | 27 |
| PUV   .85  16.2 | | | | | | | | |
| SAMo  1.1   61 | | S40.2 | S81 | S.06 | 5 | 98 | " | 26 |
| PAMo  .85   47 | | | | | | | | |
| SDX   .85  .06 | | S40.4 | S79 | S.06 | 6 | 99 | " | 24 |
| PDX   1.15  .10 | | | | | | | | |
| PVCs avg pre 8  20%+ | | S41.5 | S79 | S.06 | 1 | 102 | " | 22 |
| DX ≥        .50 | | | | | | | | |
| AMo≤        10 | | S40.4 | S78 | S.06 | 3 | 95 | " | 20 |
| DX/M≥       .425 | | | | | | | | |
| DX/M≤       .125 | | S44.5 | S77 | S.04 | 0 | 96 | " | 19 |
| ALARM Durations | | S44.3 | S76 | S.04 | 0 | 105 | " | 18 |
| ALARM — If for | | | | | | | | |
| SUV    30 min | | S40.3 | S80 | S.06 | 0 | 101 | " | 16 |
| PUV    30 min | | | | | | | | |
| SAMo   30 min | | S39.2 | S82 | S.06 | 0 | 97 | " | 14 |
| PAMo   30 min | | | | | | | | |
| SDX    30 min | | S38.8 | S83 | S.06 | 0 | 97 | " | 12 |
| PDX    30 min | | | | | | | | |
| PVC's  30 min | | S37.6 | S85 | S.06 | 0 | 99 | " | 11 |
| DX     2/10 | | | | | | | | |
| AMo    2/10 | | S35.8 | S86 | S.08 | 0 | 103 | " | 9 |
| DX/M   2/10 | | | | | | | | |
| DX/M   2/10 | | S35.2 | S84 | S.08 | 0 | 101 | " | 7 |
| Baseline Data 8:00-10:00 11/29/94 / 12/01/94 Time:18:02 GWS | | | | | | | | |

FIG 49A

Recorded Modes
1st Cluster Mode measured in seconds

|     | Mo1  | Mo2  | Mo3  |
|-----|------|------|------|
| UV  | UV1  | UV2  | UV3  |
| AMo | AMo1 | AMo2 | AMo3 |
| DX  | DX1  | DX2  | DX3  |

FIG 49B

| Recorded Modes | Recorded Modes |
|----------------|----------------|
| 1st Cluster Mode | 2nd Cluster Mode | measured in seconds

|     | Mo1  | Mo2  | Mo3  | Mo4  | Mo5  | Mo6  |
|-----|------|------|------|------|------|------|
| UV  | UV1  | UV2  | UV3  | UV4  | UV5  | UV6  |
| AMo | AMo1 | AMo2 | AMo3 | AMo4 | AMo5 | AMo6 |
| DX  | DX1  | DX2  | DX3  | DX4  | DX5  | DX6  |

FIG 49C

| Inferred Modes | Recorded Modes | Recorded Modes |
|----------------|----------------|----------------|
| 3rd Cluster Mode | 1st Cluster Mode | 2nd Cluster Mode | measured in seconds

|     | Mo7  | Mo8  | Mo9  | Mo1  | Mo2  | Mo3  | Mo4  | Mo5  | Mo6  |
|-----|------|------|------|------|------|------|------|------|------|
| UV  | UV7  | UV8  | UV9  | UV1  | UV2  | UV3  | UV4  | UV5  | UV6  |
| AMo | AMo7 | AMo8 | AMo9 | AMo1 | AMo2 | AMo3 | AMo4 | AMo5 | AMo6 |
| DX  | DX7  | DX8  | DX9  | DX1  | DX2  | DX3  | DX4  | DX5  | DX6  |

FIG 49D

Inferred Modes    Recorded Modes    Recorded Modes measured in seconds

| Avgs | 3rd Cluster Mode | 1st Cluster Mode | 2nd Cluster Mode |
|---|---|---|---|
| UV | Fr UV7 to UV9 | Fr UV1 to UV3 | Fr UV4 to UV6 |
| AMo | Fr AMo7 to AMo9 | Fr AMo1 to AMo3 | Fr AMo4 to AMo6 |
| DX | Fr DX7 to DX9 | Fr DX1 to DX3 | Fr DX4 to DX6 |

FIG 49E

Inferred Modes    Recorded Modes    Recorded Modes measured in seconds

ALARM Levels

| | 3rd Cluster Mode | 1st Cluster Mode | 2nd Cluster Mode |
|---|---|---|---|
| UV | *1.15=SUV<br>Fr UV 7 to 9<br>* .85=PUV | *1.15=SUV<br>Fr UV 1 to 3<br>* .85=PUV | *1.15=SUV<br>FR UV 4 to 6<br>* .85=PUV |
| AMo | *1.10=SAMo<br>AMo7 to 9<br>* .90=PAMo | *1.10=SAMo<br>AMo 1 to 3<br>* .90=PAMo | *1.10=SAMo<br>AMo 4 to 6<br>* .90=PAMo |
| DX | * .90=SDX<br>DX 7 to 9<br>*1.10=PDX | * .90=SDX<br>DX 1 to 3<br>*1.10=PDX | * .90=SDX<br>DX 4 to 6<br>*1.10=PDX |

FIG. 50

HEALTHY Male  AMo=27  DX=.16

| secs | bpm | | Num |
|------|-----|---|-----|
| .64 | 94 | x | 1 |
| .66 | 91 | x x | 4 |
| .68 | 88 | xx xx  x  I xxx | 15 |
| .70 | 86 | x  I xxI  xxI I | 12 |
| .72 | 83 | I x xxI xxx | 6 |
| .74 | 81 | xxx | 4 |
| .76 | 79 | x  x xx | 13 |
| .78 | 77 | xxx xxx I xx | 27 |
| .80 | 75 | Ix xx xxx xxI xI I xxI | 15 |
| .82 | 73 | I x | 2 |
| .84 | 71 | | |
| | | | 101 |

Time ------->

FIG. 51

UNHEALTHY Male  AMo=52  DX=.04

| secs | bpm | | Num |
|------|-----|---|-----|
| .64 | 94 | | |
| .66 | 91 | | |
| .68 | 88 | | |
| .70 | 86 | | |
| .72 | 83 | | |
| .74 | 81 | | |
| .76 | 79 | xx I I I  xx xxxxxx | 20 |
| .78 | 77 | xx I xxx | 52 |
| .80 | 75 | Ixx xxxxxx xx I xxxxxx xx xx xx I | 29 |
| .82 | 73 | I x I xxx | |
| .84 | 71 | | |
| | | | 101 |

Time ------->

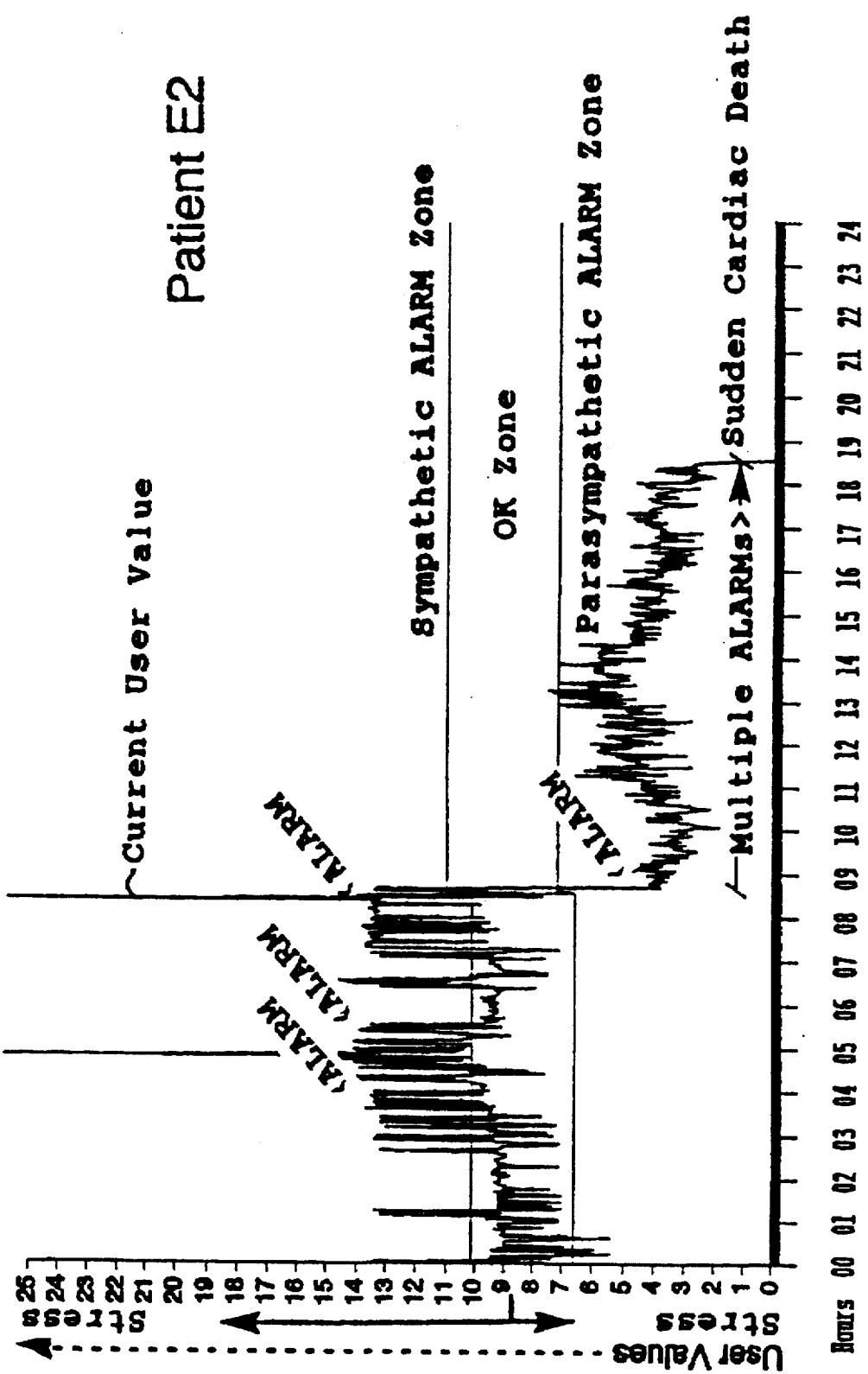

DETECTION OF ABNORMAL AND INDUCTION OF NORMAL HEART RATE VARIABILITY

RELATED APPLICATIONS

This application is a continuation of the patent application of Golosarsky et al filed Jun. 7, 1995, Ser. No. 08/482,980, now abandoned, which is a Continuation-in-Part of the application of Boris Golosarsky, Nicholas Wood, and F. Eugene Davis IV filed Jul. 13, 1994, Ser. No. 08/274,321, now abandoned which is a continuation of the application of Boris Golosarsky filed Oct. 6, 1992, Ser. No. 07/957,611, now abandoned. Said applications are incorporated herein by reference.

TECHNICAL FIELD

This invention relates to the detection of normal and abnormal heart rate variability and the induction of normal heart rate variability. More particularly, the invention relates to methods and apparatus for the detection of a user's heart rate variability that we believe is indicative of a user's sympathetic/parasympathetic stress balance, or distress imbalance.

The invention also relates to heart monitoring devices used by individuals monitored in hospital intensive care units; by user's after discharge from a hospital intensive care unit; and by users when exercising to let them know that their stress state is optimal for conditioning their bodies.

The invention further relates to control of a pacemaker or cardioverter defibrillator with a pacemaker so that when the user's heart rate is abnormal and distressful, according to the invention, a pacemaker or cardioverter defibrillator with a pacemaker induces a heart rate with a pseudo-normal or patient recorded variability for each particular user.

The invention still further relates to a pacemaker that induces pseudo-normal or patient recorded heart rate variability.

BACKGROUND ART

The normal heart rhythm is slightly irregular. Generally, normal irregularity of the heart's rhythm reflects the permanent adaptation of the human body to the environment. In this context the first sign of an impaired heart rhythm is either a persistent increase or a persistent decrease in the variability of the heart's rhythm. Sometimes the change in the heart's rhythm alternates between increases and decreases in the variability of the heart's rhythm, and vice versa. Prolonged increases, or decreases, and combinations thereof, can lead to cardiac ectopic events ranging from non-sustained ventricular tachycardia to cardiac arrest.

It is believed the variability of the heart's rhythm is controlled by two branches of the autonomic nervous system; the sympathetic branch and the parasympathetic branch. The sympathetic branch increases the heart rate. Its prime function is to prepare the body for stress, the so-called "fight or flight response". The parasympathetic branch decreases the heart rate as when eating or sleeping.

In the Soviet Union, Rhythmography, that is the study of normal and abnormal variations in heart rhythm, was utilized extensively to determine the condition of individuals and their stress state. This was particularly true of cosmonauts. It was determined for example, that the heart rate variability of a conditioned athlete is much greater than that of person with coronary disease, that is the histogram of heart rate variation of a well conditioned athlete exhibits a broad range of variability in the Time Intervals between heart beats and a low relative Amplitude of the Mode. That is the highest number of Time Intervals recorded in a series of Time Intervals. The histogram of a person with a coronary disease exhibits a narrow range of variability and a high relative Amplitude of the Mode, that is the peak of the histogram.

Applicant, Boris Golosarsky, previously received two patents in the Soviet Union, namely; SU-1683679 for an apparatus, which enables a physician to determine the arithmetic Mean, the Mode, the relative Amplitude of the Mode, and the range of variability of a subject. In the second patent in the Soviet Union, SU-1769894, he disclosed how these measurements may be utilized together with electrosleep to treat post myocardial infarction e.g. heart attack patients.

Polar Electro Oy of Finland has a patented apparatus comprised of a chest strap with a two lead ECG signal sensor and transmitter, which transmits the heart beat Time Intervals to a wrist mounted unit that can be conveniently used in this invention. See U.S. Pat. Nos. 4,625,733, Des. 278, 746, and Des. 287,403.

Pulse sensors of various types may also be used to detect the Time Interval between heart beats, (Start-of-Systole to Start-of-Systole, SOS), is essentially equal to the Time Interval between RR peaks in an electrocardiogram, (ECG).

DISCLOSURE OF THE INVENTION

Definitions

Data sources: ECG (RR) Time Intervals or pulse wave Start-of-systole to Start-of-systole (SOS) Time Intervals from the hardware sources discussed elsewhere. (Note: RR and SOS Time Intervals are used interchangeably to indicate the Time Interval between heart beats. 60 seconds divided by the Timer Interval in seconds equals the beats per minute.)

Time Interval: A Time Interval is the duration of time between heart beats, preferably measured to an accuracy of 20 milliseconds, 0.02 seconds. The accuracy of the Time Interval can range from 15 milliseconds to 30 milliseconds.

Time Segment: A Time Segment is a series of heart beats can vary in length from 51 Time Intervals to 301 Time Intervals. The preferred default setting is 101 Time Intervals.

Mode, [Mo]: The Mode is the Time Interval occurring most often in a Time Segment. For each Mode in a Time Segment there are recorded values for UV, AMo, and DX. (See below).

Cluster Mode: A Cluster Mode is a group of Modes occurring in a plurality of adjoining successive Time Segments. For each Cluster Mode there are recorded values for UV, AMo, and DX. (See below).

Amplitude of the Mode, [AMo]: The Amplitude of the Mode is the largest number of identical Time Intervals occurring in a Time Segment divided by the total number of Time Intervals in said Time Segment, which is expressed as a percentage. (e.g. 70 for 70 Time Intervals out of 101 Time Intervals.)

Delta X, [DX]: Delta X is the difference between the longest value for a Time Interval in a Time Segment and the shortest value, after outliers, (see below) and Premature Ventricular Contractions, (PVC's) (see below), if any, have been discarded. (e.g. longest equals 0.72 seconds less shortest equals 0.64 seconds=0.08 seconds=Delta X.)

User Value is determined by the formula $$UV = \sqrt{[.5/DX]^2 + [AMo/10]^2}$$

Median [M]: The Median is the Time Interval in a Time Segment, in which there are equal number Time Intervals equal to or larger than and equal to or smaller than the Median Time Interval (e.g. the 51st Time Interval in a 101 Time Interval Time Segment.)

Time Interval, Recorded: The user's recorded Time Interval is the Time Interval between two ECG (RR) peaks, or pulse wave Start of Systole to Start of Systole, (SOS) troughs recorded by the user.

Time Interval, Inferred: An inferred Time Interval is an a Time Interval that is inferred from recorded or other inferred Time Intervals.

Recorded Baseline UV, AMo, and DX The Recorded Baseline values for UV, Amo, & DX are established during the first period monitoring the user. Preferably this a 24 hour time period, but could be shortened when required, e.g. in an emergency room. The Recorded Baseline values should be re-recorded every year. As people age their heart rhythm tends to become less variable.

Recorded and Inferred Baseline UV, AMo, & DX If time does not permit recording the first 24 hours of UV, AMo, & DX, then at least 35 Time Segments are recorded and the first five Time Segments are discarded since they are part of the calibration and run-in period. The minimum acceptable recorded values for UV, AMO and DX are for three successively occurring Modes, which creates one Cluster Mode.

Premature Ventricular Contractions, [PVC's] A PVC is a Time Interval that is 20% less than the average of the previous eight Time Intervals. PVC's are discarded and new Time Intervals added until 101 Time Intervals are accumulated in a Time Segment.

Outliers are the three shortest and the three longest Time Intervals in a 101 beat Time Segment, and are discarded before calculations are made for UV, AMo and DX.

Normalized Baseline Values UV, AMo, & DX, If the user's Recorded Baseline Values-for UV, AMo, & DX are judged to be abnormal, then the variable heart rhythm of an individual most nearly matching the user's age, sex, race, build and athletic condition is substituted.

User A user is anyone whose Time Intervals are recorded.

OK: The user's physical condition is normal and not stressed.

Caution: The user has a potentially unhealthy stress condition.

ALARM 1 is present when the user's current values for UV, AMo or DX indicate sympathetic, parasympathetic, mixed sympathetic/parasympathetic over activity, or PVC's, for a predetermined number of Time Segments or a predetermined period of time.

ALARM 2 is present when no pulse is detected for ten or more seconds and the galvanic skin response sensor indicates the ECG electrodes or the pulse sensor is in contact with the user.

Motion Sensor

A transducer detects a range of motions from, no motion, to slight motion, to moderate motion to heavy motion and over load.

No motion for a predetermined period of time and a heart or pulse rate indicates a Comatose ALARM. Slight motion and a heart or pulse rate indicate sleep. Heavy motion indicates exercise and over load (spike) followed by no motion, indicates a fall.

The invention provides for the automatic detection of the user's functional and stress states based on the on-line recording of the Median, [M], one or more Cluster Modes, [CMo], the Amplitude of the Mode, [AMo], and Delta X, [DX], and User Value, [UV], recorded over successive Time Segments.

19 formulas are used to determine the user's stress status and possible ALARM, Caution, and normal OK stress condition. The multiplier factors and time durations of the 19 formulas are programmable by the user's health care provider to suit the individual user.

Cardiac Arrest ALARM

If no Time Intervals are detected for ten or more seconds and the galvanic skin response sensor indicates the ECG electrodes or the pulse sensor is in contact with the user, then this is a Cardiac Arrest ALARM.

Comatose ALARM

If Time Intervals are detected but no motion is detected for 30 or more minutes, then this is a Comatose ALARM

PVC ALARM

[1] If a Time Interval differs from the average of the previous eight Time Intervals by 50% or more, 20 or more times in a single 101 Time Interval Time Segment, for 10 minutes or longer, then this is a PVC ALARM.

AMo Sympathetic ALARM

[2] If the current value for AMo is greater than the user's baseline value for AMo for any Cluster Mode, times a predetermined multiplier factor for a predetermined number of minutes, then this is an AMo Sympathetic ALARM.

AMo Parasympathetic ALARM

[3] If the current value for AMo is lesser than the user's baseline value for AMo for any Cluster Mode, times a predetermined multiplier factor for a predetermined number of minutes, then this is an AMo Parasympathetic ALARM.

DX Sympathetic ALARM

[4] If the current value for DX is lesser than the user's baseline value for DX for any Cluster Mode, times a predetermined multiplier factor for a predetermined number of minutes, then this is an DX Sympathetic ALARM.

DX Parasympathetic ALARM

[5] If the current value for DX is greater than the user's baseline value for DX for any Cluster Mode, times a predetermined multiplier factor for a predetermined number of minutes, then this is an DX Parasympathetic ALARM.

Mixed Sympathetic/Parasympathetic ALARM-Long Term

[6] Any combination of a Sympathetic ALARM, [2], and Parasympathetic ALARM, [3], for a predetermined number of minutes is a Mixed Sympathetic/Parasympathetic ALARM-Long Term.

Mixed Sympathetic/Parasympathetic ALARM-Short Term

[7] Any combination of a Sympathetic ALARM, [2][4], and a Parasympathetic ALARM, [3][5] in 101 Time Interval Time Segment, in two or more times in any continuous grouping of ten Time Segments is a Mixed Sympathetic/Parasympathetic ALARM-Short Term.

UV Sympathetic ALARM

[8] If the current value for UV is greater than the user's baseline value for UV for any Cluster Mode, times a predetermined multiplier factor for a predetermined number of minutes, then this is a UV Sympathetic ALARM.

UV Parasympathetic ALARM

[9] If the current value for UV is lesser than the user's baseline value for UV for any Cluster Mode, times a predetermined multiplier factor for a predetermined number of minutes, then this is an UV Parasympathetic ALARM.

UV Mixed Sympathetic/Parasympathetic ALARM-Long Term

[10] Any combination of a UV Sympathetic ALARM, [8], and a UV Parasympathetic ALARM, [9], for a predetermined number of minutes is a UV Mixed Sympathetic/Parasympathetic ALARM-Long Term.

UV Mixed Sympathetic/Parasympathetic ALARM-Short Term

[11] Any combination of a UV Sympathetic ALARM, [8], and a UV Parasympathetic ALARM,[9] in 101 Time Interval Time Segment, in two or more times in any continuous grouping of ten Time Segments is a UV Mixed Sympathetic/Parasympathetic ALARM-Short Term.

The Cardiac Arrest ALARM, Comatose ALARM, and the PVC ALARM and the next six formulas for ALARMS and Cautions are absolute, and not dependant on the user's baseline values.

Sympathetic ALARM-Type II

[12] If DX divided by the Median is equal or less than 0.125, and in two or more times in any continuous grouping of ten Time Segments, then this is a Sympathetic ALARM-Type II.

Parasympathetic ALARM-Type II

[13] if DX divided by the Median is equal or greater than 0.425, in two or more times in any continuous group of ten Time Segments, then this is a Parasympathetic ALARM-Type II.

Parasympathetic ALARM-Type III

[14] If DX is equal or greater than 0.50 in two or more Time Segments in any continuous group of ten Time Segments, then this is Parasympathetic ALARM-Type III.

Parasympathetic ALARM-Type IV

[15] If AMo is equal or less than 10 in two or more Time Segments in any continuous grouping of ten Time Segments, then this is a Parasympathetic ALARM-Type IV.

Sympathetic Caution-Long Term

[16] If DX equals 0.06 or less for one hour or longer, then this is a Sympathetic Caution-Long Term.

Caution-Short Term

[17] If AMo and DX vary directly with each other in a single or adjoining Cluster Modes for one hour or longer, then this is a Caution-Short Term.

If the Median and the Mode differ from each other in a 101 Time Interval Time Segment by 20% or more, than this a case of non-stationarity and the values generated are discarded and not included in calculations.

It is believed that other formulas characterizing the histogram might be used after further analysis of the data. These could be the width at half maximum of the histogram instead of DX, the use of Standard Deviation instead of DX, and the Amplitude of the Median instead of AMo in the 17 formulas where applicable.

The user's functional and stress states may be displayed to the user or a health care provider in all alphanumeric fashion. This enables the user or health care provider to determine the user's stress status substantially instantaneously at any time or place, and to attain a state of effective cardiovascular fitness.

The inventors believe that the triangle of the histogram indicated by formulas [8] and [9], e.g. the sharpness, or flatness of the histogram, (is equivalent to the Q of a resonant circuit), is a measure for each Cluster Mode that indicates that the user is in a normal autonomic balance or homeostasis between sympathetic and parasympathetic control of the user's heart rate variability.

Abnormal deviation of these functions above or below those recorded in both healthy and unhealthy subjects indicate abnormal stress and thus cardiac distress.

Detection of abnormal heart rate variability in a series of Time Segments can therefore be used to signal a health care provider, or pacemaker, or cardioverter defibrillator with a pace maker, to intervene according to the invention, or to indicate that the heart is being over stressed by the particular activity (e.g. physical, psychogenic) being engaged in.

Also according to the invention, a pacemaker or a cardioverter defibrillator with a pacemaker can be programmed to provide a normal, therapeutic heart rate variability rather than an unnatural steady beat as in the prior art. This may be accomplished by, (1) recording the user's normal, variable heart rate, or (2) the normal, variable heart rhythm of an individual most nearly matching the user's age, sex, race, build and athletic condition, or (3) using a random pulse generator that produces a normal, variable histographic heart rate, all in conjunction with an impedance pacemaker, (a pacemaker that detects respiration) and a galvanic skin response detector.

OBJECTS OF THE INVENTION

It is the therefore an object of this invention to provide a method and apparatus for determining the user's stress state.

Another object of the invention is to provide such apparatus, which allows the user to exercise in a stress state which will, bring about a maximum conditioning effect.

A further object of the invention is to provide such apparatus and method that the user will be notified of non-optimal or an ALARM or Caution distress state.

Still another object of the invention is to detect stress and distress states from simple parameters derived from the recording of a plurality of durations of successive Time Intervals between heart beats.

Yet another object of the invention is to detect cardiac distress.

Still another object of the invention is to detect abnormal heart rate variability over a relatively short period of time and to signal this abnormality to a health care provider, or a pacemaker or a cardioverter defibrillator with a pacemaker, to initiate intervention.

A still further object of the invention is to cause a pacemaker or cardioverter defibrillator with a pacemaker, to pace a heart with a normal heart rate variability.

Other objects of the invention will in part be obvious and will in part appear hereinafter.

The invention accordingly comprises a method comprising several steps and the relation of one or more of such steps with respect to each of the others, and the apparatus embodying features of construction, elements, and arrangements of parts, which are adapted to effect such steps, all as exemplified in the following detailed disclosure.

The scope of the invention will be indicated in the claims.

For a fuller understanding of the nature and objects of the invention, reference should be had to the following detailed description taken in connection with the drawings forming a part thereof.

7

BRIEF DESCRIPTION OF THE DRAWINGS

For a fuller understanding of the nature and objects of the invention reference should be had to the following detailed description taken in connection with the accompanying drawings in which:

FIGS. 1, 1A and 1B are diagrams showing the electrocardiogram recording of a subject and the subject's pulse waves showing that the RR intervals in the electrocardiogram are substantially equal to the corresponding intervals between start of systole;

FIG. 5 is a detailed block diagram of the apparatus shown in FIG. 3;

FIG. 6 is a detailed block diagram of a sports watch apparatus according to the invention;

FIG. 7 is a block diagram of multiple patient monitoring apparatus according to the invention;

FIG. 8 is a detailed view of Screen A of FIG. 7;

FIG. 9 is a detailed view of Screen B of FIG. 7;

FIG. 49A is a diagram showing recorded values of the user's value (UV), Amplitude of the Mode (AMo), and Delta X (DX) of the shortest mode, the next shortest mode, and the third shortest mode of three successively recorded time segments of 101 heart beats comprising a cluster mode according to the invention;

FIG. 49B, similar to FIG. 49A, also includes the next three successively longer modes (Mo);

FIG. 49C is a diagram showing how (UV), (AMo), and (DX) from even shorter modes may be inferred from the measurements indicated in FIG. 49B;

FIG. 49D is a diagram indicating how, according to the invention, the average (UV), average (AMo), and average (DX) is calculated for each cluster mode;

FIG. 49E is a diagram showing how alarm levels for (UV), (AMo), and (DX) are preferably calculated from recorded and inferred modes of a user or if the user's recording is not available from a matched subject;

FIG. 50 is a diagram of heart rate versus time over 101 heart beats for a normal healthy male age 63;

FIG. 51 is a similar diagram for an unhealthy male age 51;

8

Figure 53:
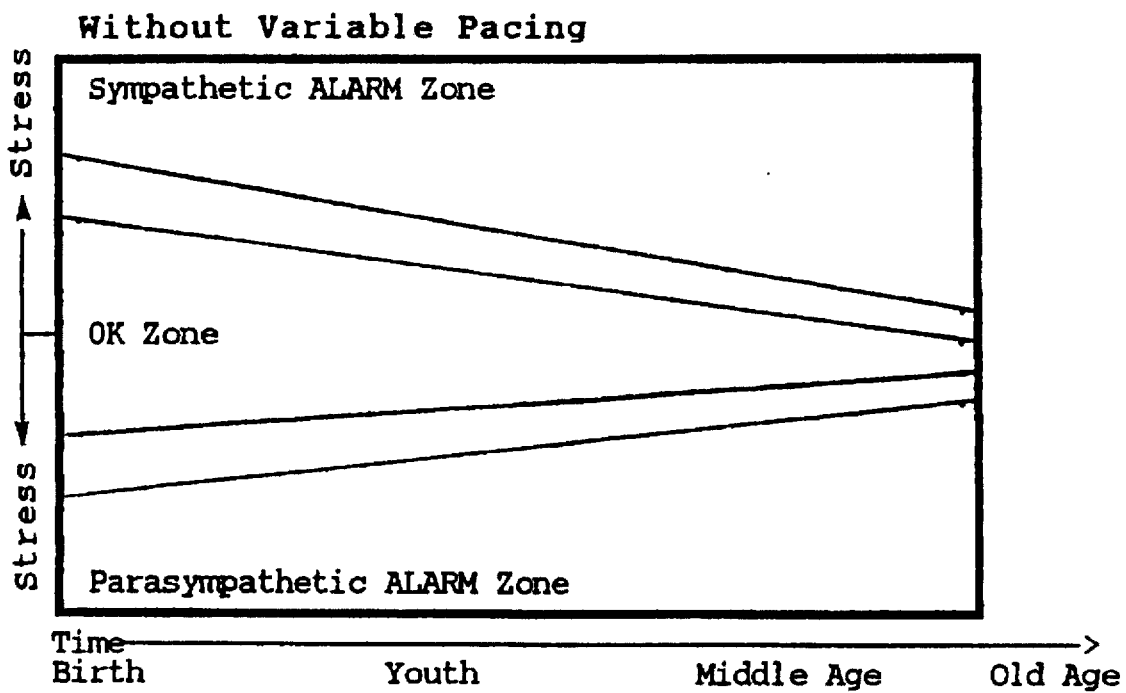
Figure 54:
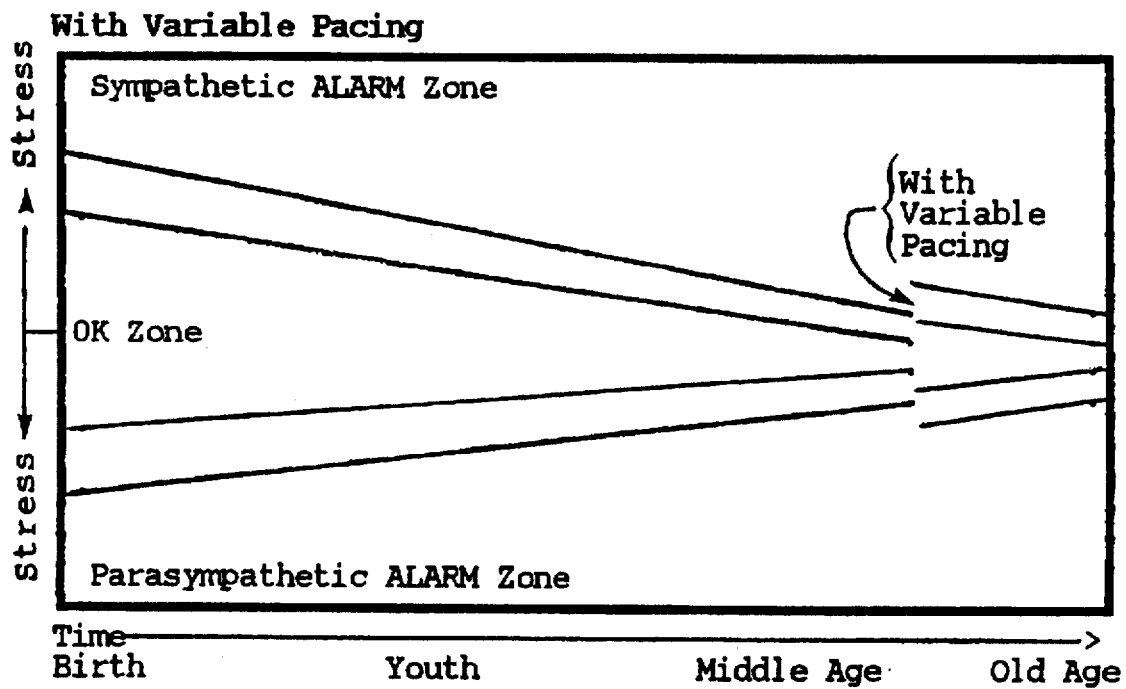

FIG. 53 is a diagram showing how the alarm zones of heart rate variability narrow the OK zone over a human's life time;

FIG. 54 is a diagram, similar to FIG. 53, showing how with variable pacing, according to the invention, the OK zone maybe enlarged to be similar to that of a younger subject; and FIG. 55 is a record of user values (UV) of a cardiac patient showing how user value alarms indicating sympathetic nervous system over activity were repeatedly activated more than 17 hours prior to sudden cardiac death and how a switch from a sympathetic alarm condition to a parasympathetic alarm condition occurred approximately 10 hours before sudden cardiac death and continued during this entire period until sudden cardiac death.

The same reference characters refer to the same elements throughout the several views of the drawings.

BEST MODE FOR CARRYING OUT THE INVENTION

Figure 1:
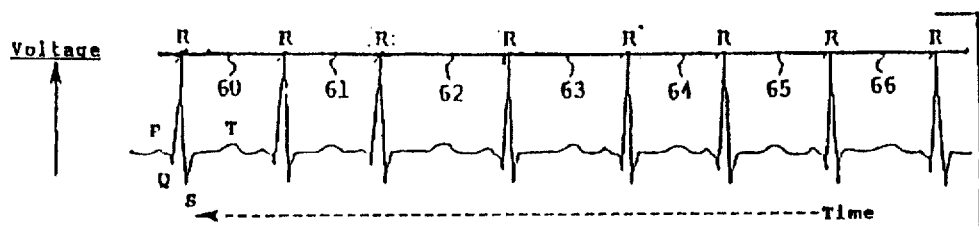

As shown in FIGS. 1A and 1B, every heart beat is composed of an electrical wave pattern called the PQRST wave. The letters indicate the important points in the wave pattern, and is generated by an electrocardiogram monitor or ECG. The letter "R" designates the peak of the PQRST wave. The Time Intervals between RR peaks are indicated at 60 to 61, 61 to 62, 62 to 63, etcetera, etcetera.

Also as shown in FIGS. 1A and 1B for pulse detection, the Time Intervals between the Start of Systole to the Start of Systole, SOS. The Time Intervals between SOS troughs are indicated at 70 to 71, 71 to 72, 72 to 73, etcetera, etcetera.

The ECG RR Time Intervals have substantially the same time duration as the pulse SOS Time Intervals and occur about a half second later than the RR Time Intervals.

Figure 2:
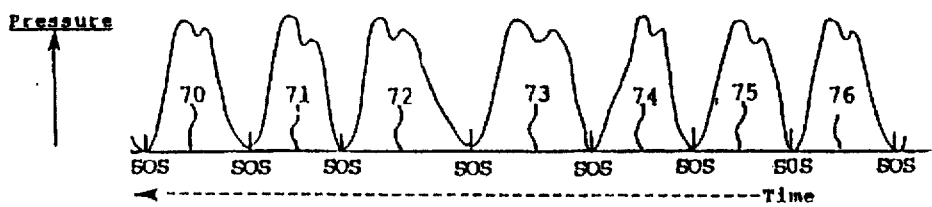
FIG. 2 is a histogram of the numbers of equal time intervals between heart beats recorded from a normal subject.

FIG. 2 is a typical histogram of a 101 Time Intervals in a Time Segment. The outliers, e.g. the three longest and the three shortest Time Intervals are deleted. Delta X, [DX], is the difference between the longest Time Interval remaining and the shortest Time Interval remaining. The Mode, [Mo], is the Time Interval occurring most often in a Time Segment. The Amplitude of the Mode, [AMo], is the largest number of identical Time Intervals occurring in a Time Segment divided by the total number of Time Intervals in said Time Segment. The Median, [M], is the Time Interval in a Time Segment, in which there are equal numbers of Time Intervals equal to or larger and equal to or smaller than the Median Time Interval. As shown in FIG. 2 of a normal user, the Mode and the Mean are the same.

Figure 3:
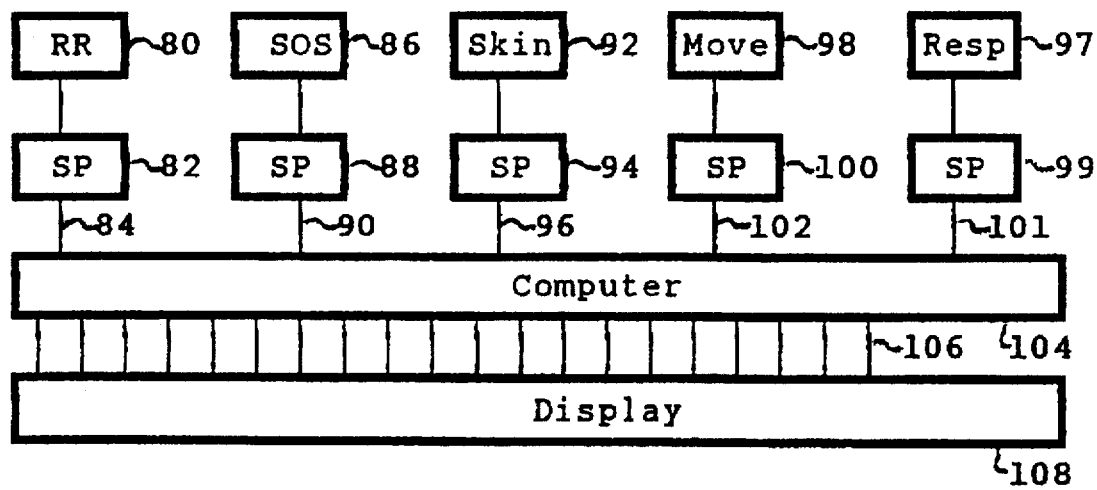
FIG. 3 is an overall block diagram of apparatus according to the invention.

In FIG. 3, the RR Time Interval data 80 is received from an RR Time Interval sensor and the signal is processed 82, and transferred 84 to a computer 104. Also SOS Time Interval data 90 is received from an SOS Time Interval sensor and the signal processed 88, and transferred 90 to a computer 104. Also, data from a galvanic skin response sensor 92 is received and the signal processed 94, and transferred 96 to a computer 104. Also data from a motion sensor 98 is received and the signal processed 100, and transferred 102 to a computer 104. Also data from a respiratory sensor 97 and the signal processed 99, and transferred to a computer.

The results of the computer's analysis is transferred 106 to a display 108.

Figure 4:
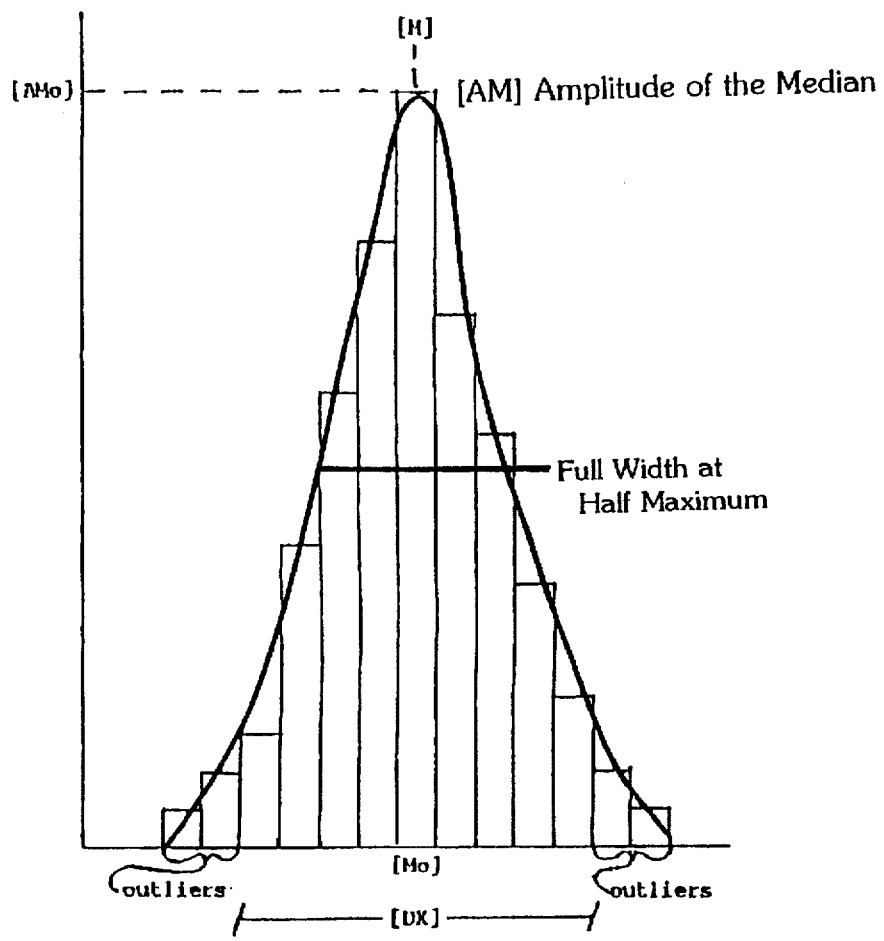
FIG. 4 is a diagram showing how FIGS. 4A, 4B, and 4C maybe placed together to form FIG. 4 which is a flow chart showing the processing of a preselected number of heart beat intervals to determine the seventeen alarm conditions utilized in the invention.
Figure 4A:
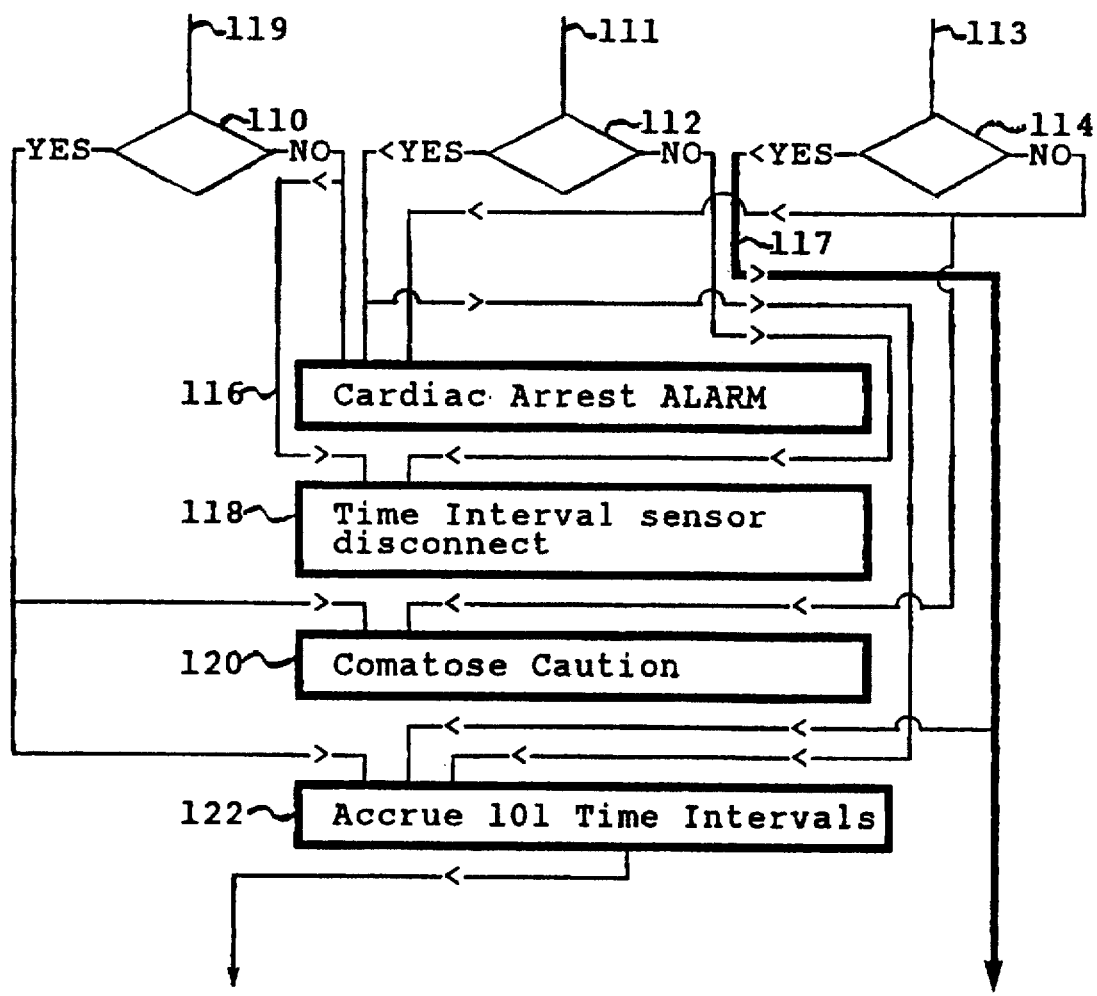
Figure 4B:
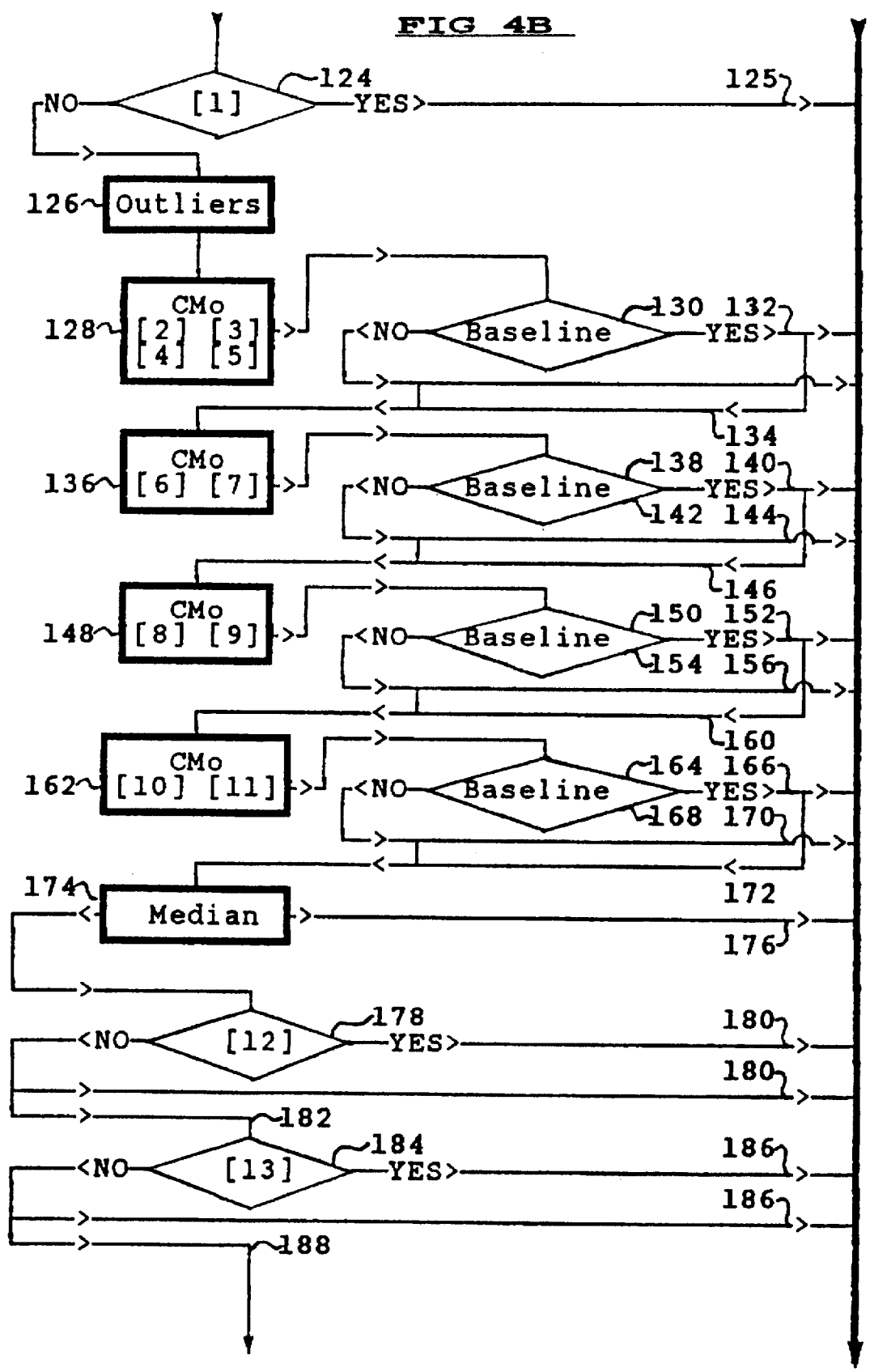

FIG. 4 is a diagram of FIGS. 4A, 4B, and 4C.

Figure 48:
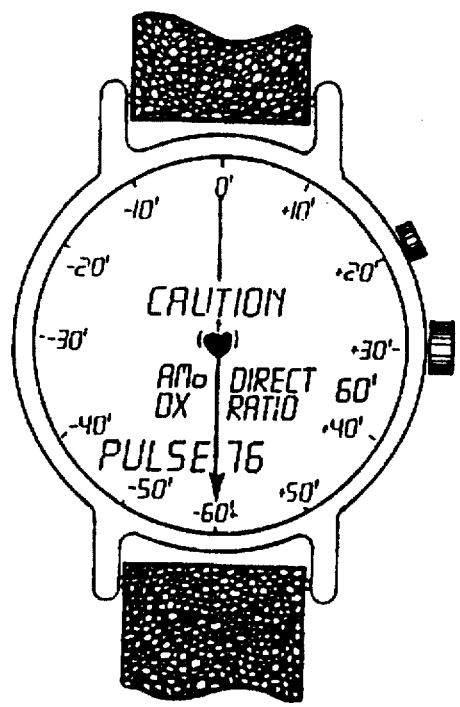

In FIG. 4A, each of the following 17 formulas is assigned a separate memory which stores four hours of ALARM, Caution and OK data in the devices diagramed in FIG. 5 and FIG. 6, and 48 hours of data in the device diagramed in FIGS. 7, 8, 9 and 10.

In FIG. 4A, RR Time Interval data 119, or SOS Time Interval data 119 is analyzed to determine if Time Interval data is being received. Also, galvanic skin response data 111 is analyzed. Motion and non-motion data 113 is analyzed and the results transferred 117 to memory 212.

If no Time Intervals are detected 110 and no motion is detected 114, and the galvanic skin response sensor data indicates the Time Interval sensor is in contact with the user 112, and this situation occurs for 10 seconds or longer, then this is a Cardiac Arrest ALARM 116.

If no Time Interval data is detected 110 and the galvanic skin response sensor 114 records no contact with the user, then the Time Interval sensor is disconnected from the user 118.

If no Time Interval data is detected 110 and the motion sensor has not recorded any movement for a predetermined period of time 114, then this a Comatose ALARM 120.

Then 101 Time Intervals are accumulated in a Time Segment for further analysis 122.

Formula [1] processes a 101 Time Intervals in a Time Segment. If 20 or more PVC's are detected 124 the data is transferred 125 to memory 212. If 20 or more PVC's per Time Segment occur for a predetermined period of time then a PVC ALARM is detected. If 1 to 19 PVC's are detected, they are discarded and the next succeeding Time Intervals equal to the number discarded, replace the discarded Time Intervals until 101 Time Intervals are accumulated 119.

In FIG. 4B a Time Segment of 101 Time Intervals 122 are analyzed by the following formulas:

If no PVC's are detected, then the three longest and the three shortest Time Intervals are deleted as outliers 126.

Formulas for AMo [2][3] and DX [4][5] for each current Cluster Mode in which they occur are calculated 128 and compared with the user's recorded baseline values for AMo and DX 130. If one or more ALARMs are detected the data is transferred 132 to the appropriate memory assigned to formulas [2][3][4] and [5] 212. If one or more ALARMs occurs for a predetermined period of time, interrupted by single, non-contiguous OK Time Segments, if any, then one or more of four ALARMs are detected, e.g. An Amo Sympathetic ALARM [2], an AMo Parasympathetic ALARM [3], a DX Sympathetic ALARM [4], a DX Parasympathetic ALARM [5], as the case may be 130. If an ALARM is detected and if no ALARM is detected 134, the 101 Time Intervals in the Time Segment 122 are analyzed by the next formula [6] 136.

If a combination of Sympathetic ALARMs, [2] and [4], and Parasympathetic ALARMs, [3] and [5] occur for a predetermined period of time, interrupted by single, non-contiguous OK Time Segments,if any, then a Mixed Sympathetic/Parasympathetic ALARM-Long Term [6] is detected 138. In an ALARM is detected by formula [6], the data is transferred 140 to the memory assigned to formula [6] 212. If an ALARM is detected and if no ALARM is detected 146, the data is transferred 144 to the appropriate memory assigned to formula [6], and the 101 Time Intervals in the Time Segment 122 are analyzed by the next formula [7] 148.

If a combination of Sympathetic ALARMs, [2] and [4], and Parasympathetic ALARMs, [3] and [5] occur in a single Time Segment, in a predetermined percentage of 10 continuous Time Segments, then a Mixed Sympathetic/Parasympathetic ALARM-Short Term [7] is detected 142. If an ALARM is detected by formula [7], the data is transferred 144 to the memory assigned to formula [7] 212. If an ALARM is detected and if no ALARM is detected 146 the data is transferred 144 to the appropriate memory assigned to formula [7], and the 101 Time Intervals in the Time Segment 122 are analyzed by the next formula [8] 148. The formula for UV Sympathetic [8] for each current Cluster Mode in which it occurs is calculated and compared with the user's recorded baseline values for UV 150. If an ALARM occurs for a predetermined period of time, interrupted by single, non-contiguous OK Time Segments, if any, then an ALARM is detected, e.g. a UV Sympathetic Alarm [8] 148. If an ALARM is detected by formula [8], the data is transferred 152 to the memory assigned to formula [8] 212. If an ALARM is detected and if no ALARM is detected 160, the data is transferred 152 to the appropriate memory assigned to formula [8], and the 101 Time Intervals in the Time Segment 122 are analyzed by the next formula [9] 148.

The formula for UV Parasympathetic [9] for each current Cluster Mode in which it occurs is calculated and compared with the user's recorded baseline values for UV 154. If an ALARM occurs for a predetermined period of time, interrupted by single, non-contiguous OK Time Segments, if any, then an ALARM is detected, e.g. a UV Parasympathetic Alarm [9] 148. If an ALARM is detected by formula [9], the data is transferred 156 to the memory assigned to formula [9] 212. If an ALARM is detected and if no ALARM is detected 160, the data is transferred 156 to the appropriate memory assigned to formula [9], and the 101 Time Intervals in the Time Segment 122 are analyzed by the next formula [10] 162.

If a combination of UV Sympathetic ALARMs [8] and UV Parasympathetic ALARMs [9] occur for a predetermined period of time, interrupted by single, non-contiguous OK Time Segments, if any, then a Mixed UV Sympathetic/Parasympathetic ALARM-Long Term [10] is detected 162. If an ALARM is detected by formula [10], the data is transferred 166 to the memory assigned to formula [10] 212. If an ALARM is detected and if no ALARM is detected 172, the data is transferred 166 to the appropriate memory assigned to formula [7], and the 101 Time Intervals in the Time Segment 122 are analyzed by the next formula [11] 162.

If a combination of UV Sympathetic ALARMs [8] and UV Parasympathetic ALARMs [9], occur in a single Time Segment, in a predetermined percentage of 10 continuous Time Segments, then a Mixed UV Sympathetic/Parasympathetic ALARM-Short Term [11] is detected 162. If an ALARM is detected by formula [11], the data is transferred 170 to the memory assigned to formula [11] 212. If an ALARM is detected and if no ALARM is detected 172, the data is transferred 170 to the appropriate memory assigned to formula [7], and the 101 Time Intervals in the Time Segment 122 are analyzed and the Median, [M], is calculated 174.

The Median, [M], Time Interval of the current Time Segment is calculated 174 and the Time Intervals in the Time Segment 122 are analyzed by the next formula [12] 178.

If within a Time segment, DX divided by the Median, [M], 174 equals or is less than 0.125 the data is transferred 180 to the memory assigned to formula [12] 212. If within a Time Segment, DX divided by the Median equals or is less than 0.125 occurs in a predetermined percentage of 10 continuous Time Segments, then a Sympathetic Type II ALARM [12] 178 is detected. Also, if within a Time Segment, DX divided by the Median equals or is more than 0.125 but less than 0.425 182, and the data is transferred 180 to the memory assigned to formula [12] 212, and the Time Intervals in the Time Segment 122 are analyzed by the next formula [13] 184.

If within a Time Segment, DX divided by the Median, [M] 174 equals or is more than 0.425 the data is transferred 186 to the memory assigned to formula [13] 212. If within a Time Segment, DX divided by the Median equals or is more than 0.425 occurs in a predetermined percentage of 10 continuous Time Segments, then a Parasympathetic Type II ALARM [13] 184 is detected. Also, if within a Time Segment, DX divided by the Median equals or is more than 0.125 but less than 0.425 184 the data is transferred 186 to the memory assigned to formula [13] 212, and the Time Intervals in the Time Segment 122 are analyzed by the next formula [14] 190.

If within a single Time Segment, DX equals or is more than 0.50 190 the data is transferred 192 to the memory assigned to formula [14] 212. If this occurs in a predetermined percentage of 10 continuous Time Segments, then a Parasympathetic ALARM Type III [14] 190 is detected. Also, if within a Time Segment, DX is less than 0.50, the data is transferred 192 to the memory assigned to formula [14] 212, and the Time Intervals in the Time Segment 122 are analyzed by the next formula [15] 196.

If within a single Time Segment, AMo equals or is less than 10 196, the data is transferred 198 to the memory assigned to formula [15] 212. If this occurs in a predetermined percentage of 10 continuous Time Segments, then a Parasympathetic Type IV ALARM [15] 196 is detected. Also, if within a Time Segment, AMo is more than 10 200, the data is transferred 198 to the memory assigned to formula [15] 212, and the Time Intervals in the Time Segment 122 are analyzed by the next formula [16] 202.

In FIG. 4C is the continued analysis of a Time Segment of 101 Time Intervals 122 are by the, following formulas:

If DX is equal or less than 0.06 202, the data is transferred 204 to the memory assigned to formula [16] 212. If this occurs for a percentage of a predetermined period of the time, then a Sympathetic Caution-Long Term [16] 202 is detected. Also, if DX is more than 0.06 206, the data is transferred 204 to the memory assigned to formula [16] 212, and the Time Intervals in the Time Segment 122 are analyzed by the next formula [17] 208.

If AMo and DX vary directly with each other 208, the data is transferred 210 to the memory assigned to formula [17] 212. If this occurs for a percentage of a predetermined period of time, then a Caution-Short Term [17] 208 is detected. Also, if AMo and DX do not vary directly, the data is transferred 210 to the memory assigned to formula [17] 212, and the count of new Time Intervals in the next succeeding Time Segment commences 213.

In FIG. 5, A microprocessor with a date and time clock 300 gathers Time Interval data from a Time Interval sensor 80 or 86, and from a motion sensor 98 and a galvanic skin response sensor 92. ALARM, Caution and OK stress data is stored in the microprocessor memory and dated and time stamped by the date and time clock 300. The stress data accumulated for the user can be down loaded to a PC 301. Also the multiplier factors and time durations for the 17 formulas can be programmed and re-programmed by the user's health care provider 324.

The user's stress status is displayed on a liquid crystal diode 302. If the battery has less than a 20% charge a buzzer notifies the user 304.

The battery power pack 303 supplies electricity to operate the components 80 through 306.

The user's stress status is transmitted by a low power RF transmitter 306 to a receiver 308 inside the cellular telephone 312.

If the cellular telephone 312 is recharging in the cellular telephone recharge unit 314 and an ALARM is received, then the strobe light 316 is activated on the cellular telephone 312, and the voice microprocessor broadcasts 318 from the cellular telephone earpiece speaker CPR instructions, and the user's front door light starts to flash 320, and the front door is unlocked by activating an electric door strike 322, and an ALARM message is transmitted by the cellular telephone 312, first by attempting a landline connection 323 to a health care provider 324, and failing a landline connection 325, then on cellular frequencies to 313 to a health care provider 324.

In FIG. 6, A microprocessor with a date and time clock 300 gathers Time Interval data, 80 or 86, from a Time Interval sensor 80 or 86. ALARM, Caution and OK stress data is stored in the microprocessor memory and dated and time stamped by the date and time clock 300. The stress data accumulated for the user can be down loaded to a PC 301. Also the multiplier factors and time durations for the 17 formulas can be programmed and re-programmed by the user's health care provider 324.

The battery power pack 303 supplies electricity to operate the components 80 through 318.

The user's stress status is displayed on a liquid crystal diode 302, and the voice microprocessor broadcasts from a micro speaker CPR instructions 318. If the battery has less than a 20% charge a buzzer notifies the user 304.

FIG. 7 illustrates a single channel ECG apparatus for eight patient users 400 through 414 in hospital critical care units. The RR Time Interval data for each patient user and each signal processed 416 and downloaded to a central PC 418, which analyzes each user's stress status and displays this information on a monitor, FIG. 8, Screen A, FIG. 9, Screen B, and FIG. 10, Screen C.

FIG. 8, Screen A is the eight patient monitor which displays the user patient's name, room and bed number, and the current values for each user patient's UV, AMo, and DX, the PVC count, and heart rate in Beats Per Minute. In addition, Screen A displays each user patient's UV, AMo, and DX ALARM status, the setting in minutes of when an ALARM would be triggered and the number of minutes an ALARM condition, if any, has persisted. In the FIG. 8 example, user patient 8, in the current Time Segment has experienced a UV of 40.1, an AMo of 80, a DX of 0.06, 7 PVC's, which indicate a Sympathetic UV, AMo, and DX ALARM, and that this ALARM condition has persisted for 31 minutes, or one minute longer than the 30 minute ALARM set point.

If a user patient experiences an ALARM, the health care provider on duty can display an individual user's recent stress record, as illustrated in FIG. 9, Screen B.

In the left hand column are the user patient's name, room and bed designation. Below this information. Below this information are the ALARM Settings comprised of the baseline formulas for UV, AMo, and DX, the multiplier factors used to establish the user patient's Sympathetic and Parasympathetic ALARM Zones, and the values derived, which trigger all ALARM condition. Below this are the ALARM durations, which cause an ALARM to be triggered.

In the central column are displayed the user patient's values for UV, AMo, DX, and PVC's together the user patient's heart rate in BPM and the ALARM set.

In the right hand column are the time duration of each of the ALARM conditions displayed in the central column.

Figure 10:
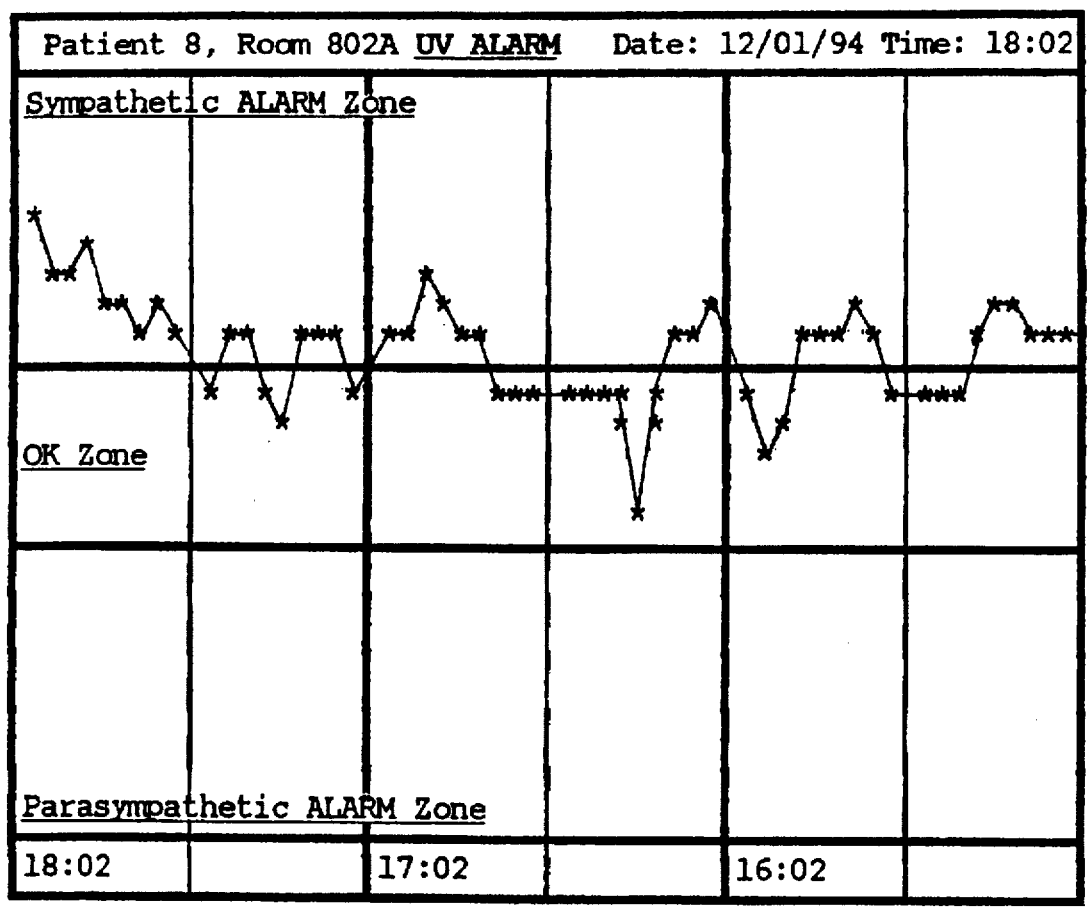
FIG. 10 is a detailed view of Screen C of FIG. 7.

The health care provider can view a graphic illustration of a user's recent stress record as illustrated in FIG. 10, Screen C.

Figure 11:
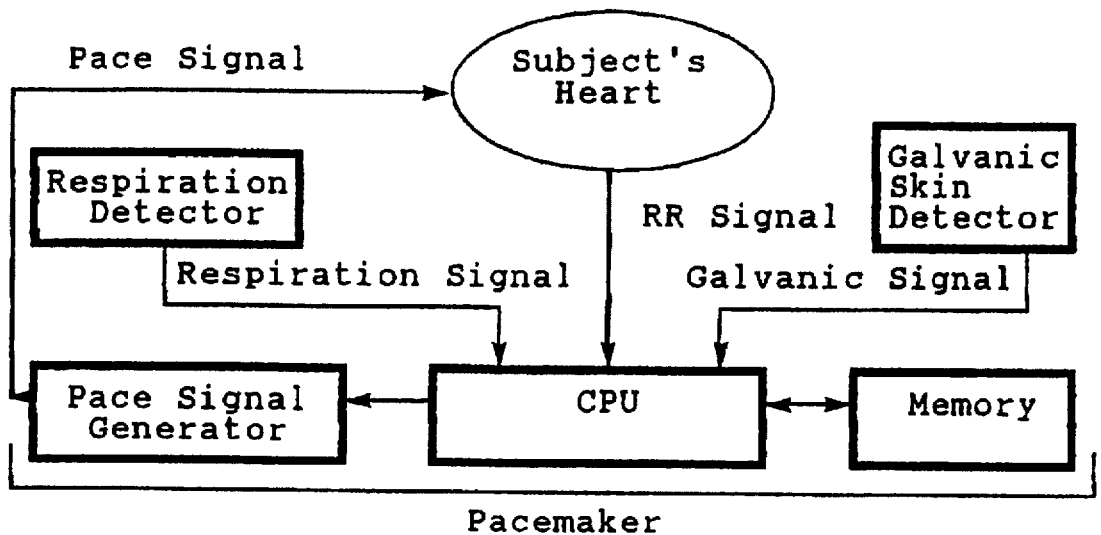
FIG. 11 is a block diagram of a pacemaker which also maybe part of a pacemaker cardiodefibrillator according to the invention.

As shown in FIG. 11, if the CPU in a cardioverter defibrillator with a pacemaker or a pacemaker detects an ALARM condition in the User's Heart, as described in FIG. 4A, 4B, and 4C, then, based on the additional data from the Respiration Detector and the Galvanic Skin Detector, the Pace Signal Generator will commence pacing the User's Heart for a predetermined period of time.

Figure 12:
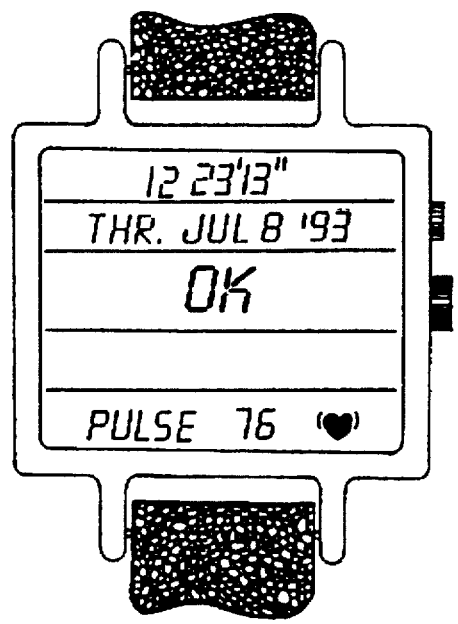
FIGS. 12 through 48 show various displays on various sports watches according to the invention.

FIG. 12 illustrates a rectilinear digital display format of the wrist unit component described in FIG. 5 and FIG. 6. The top line displays the date, the second line the time, the third line the user's stress or distress status, the fourth line the type of distress based on one or more of the 17 distress formulas discussed elsewhere, and the fifth line the user's pulse and the symbol for a heart indicating the galvanic skin response sensor is gathering pulse data from the user. In the FIG. 12 example, the user's stress/distress state is OK.

Figure 13:
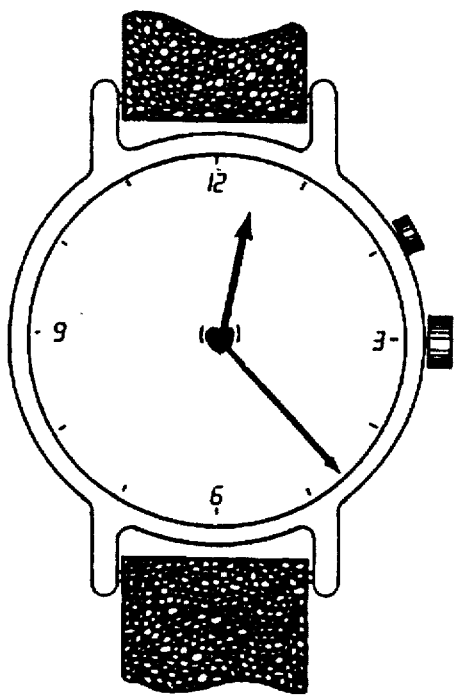

FIG. 13 illustrates an alternative round analog/digital standard watch format screen of the wrist unit component described in FIG. 5 and FIG. 6.

Figure 14:
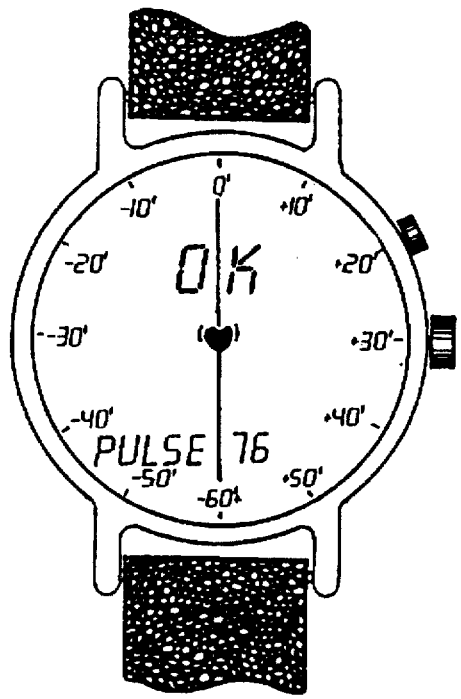

FIG. 14 illustrates the stress/distress screen on the round analog/digital standard watch format of the wrist unit component described in FIG. 5 and FIG. 6. The left hemisphere of the screen is for the display of the type of distress based on one or more of the seventeen, [1]–[17], distress formulas discussed elsewhere. The numbers from 0 at the 12 o'clock position going counterclockwise to −60 at the 6 o'clock position indicate the duration of a parasympathetic alarm in minutes. The numbers from 0 at the 12 o'clock position going clockwise to +60 at the 6 o'clock position indicate the duration of a sympathetic alarm in minutes. At the center of the two hemispheres is the symbol for a heart indicating the galvanic skill response sensor is gathering pulse data. The user's pulse is displayed at the bottom of the screen. In FIG. 14 the user's stress/distress state is OK.

Figure 15:

FIG. 15 illustrates a user's ALARM in the digital format based on the first, [1], stress formula, discussed elsewhere, and is based on 20 or more premature ventricular contractions, PVC's per Time Segment. This information is displayed on the fourth line of the digital format screen along with the type of activity, which in this example is 20 PVC's per Time Segment, and the duration of the over activity, which in this example is two out of the ten previous Time Segments.

Figure 16:
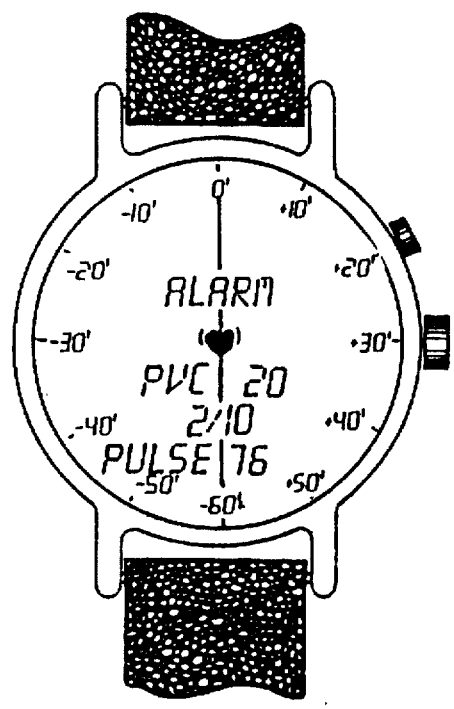

FIG. 16 illustrates a user's ALARM on the stress/distress screen of the round analog/digital standard watch based format on the first, [1], stress formula, discussed elsewhere, and is based on 20 or more PVC's per Time Segment. This information is displayed in the center of the two hemispheres of the analog/digital format screen. The type of over activity, which in this example is 20 PVC's, and the duration of the over activity, which in this example is two out of the previous ten Time Segments.

Figure 17:
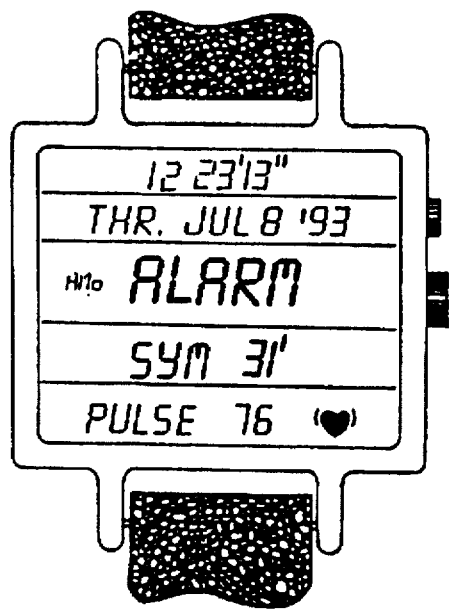

FIG. 17 illustrates a user's ALARM in the digital format based on the second, [2] stress formula, discussed elsewhere, and is based on an over active sympathetic AMo. This information is displayed on the fourth line of the digital format screen along with the type of over activity, which in this example is sympathetic, end the duration of the over activity, which in this example is 31 minutes.

Figure 18:
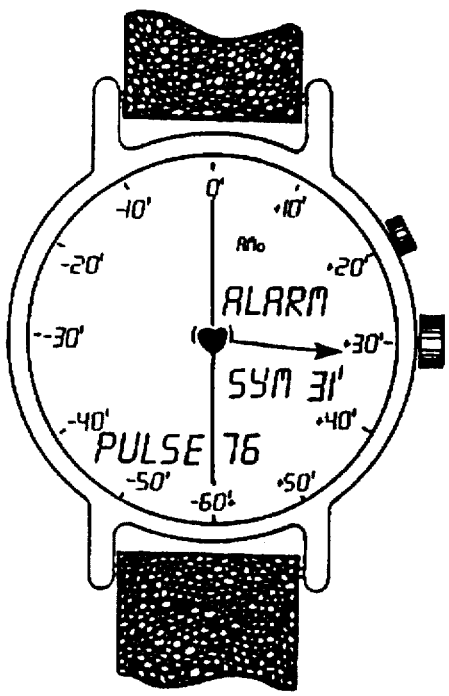

FIG. 18 illustrates a user's ALARM on the stress/distress screen of the round analog/digital standard watch based format on the second, [2] stress formula, discussed elsewhere, and is based on an over active sympathetic AMo. This information is displayed in the right hemisphere of the analog/digital format screen. The type of over activity, which in this example is sympathetic, and the duration of the over activity, which in this example is 31 minutes.

Figure 19:

FIG. 19 illustrates a user's ALARM in the digital format based on the third, [3] stress formula, discussed elsewhere, and is based on an over active parasympathetic AMo. This information is displayed on the fourth line of the digital format screen along with the type of over activity, which in this example is parasympathetic, and the duration of the over activity, which in this example is 31 minutes.

Figure 20:
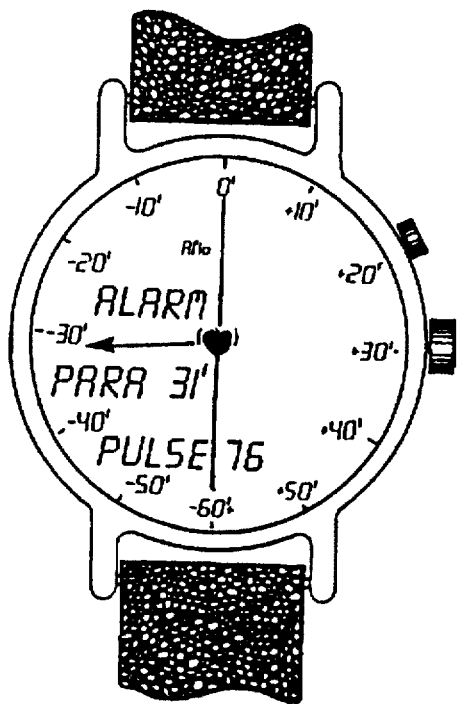

FIG. 20 illustrates a user's ALARM on the stress/distress screen of the round analog/digital standard watch based format on the third, [3] stress formula, discussed elsewhere, and is based on an over active parasympathetic AMo. This information is displayed in the left hemisphere of the analog/digital format screen. The type of over activity, which in this example is parasympathetic, and the duration of the over activity, which in this example is 31 minutes.

Figure 21:
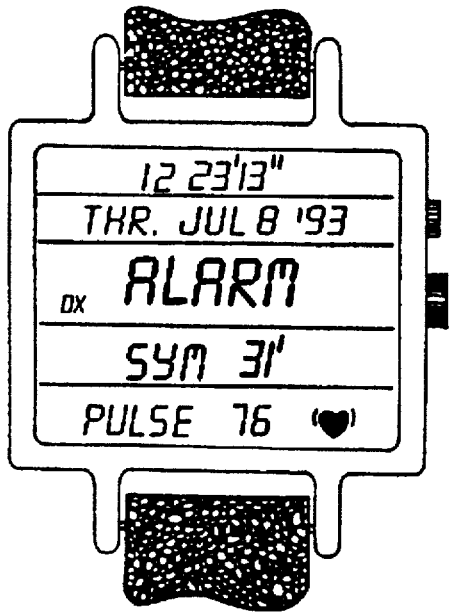

FIG. 21 illustrates a user's ALARM in the digital format based on the fourth, [4] stress formula, discussed elsewhere, and is based on an over active sympathetic DX. This information is displayed on the fourth line of the digital format screen along with the type of over activity, which in this example is sympathetic, and the duration of the over activity, which in this example is 31 minutes.

Figure 22:
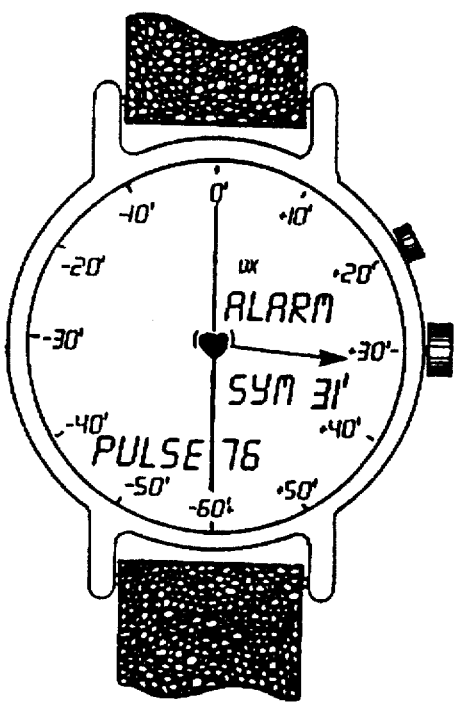

FIG. 22 illustrates a user's ALARM on the stress/distress screen of the round analog/digital standard watch based format on the fourth, [4] stress formula, discussed elsewhere, and is based on an over active sympathetic DX. This information is displayed in the right hemisphere of the analog/digital format screen. The type of over activity, which in this example is sympathetic, and the duration of the over activity, which in this example is 31 minutes.

Figure 23:
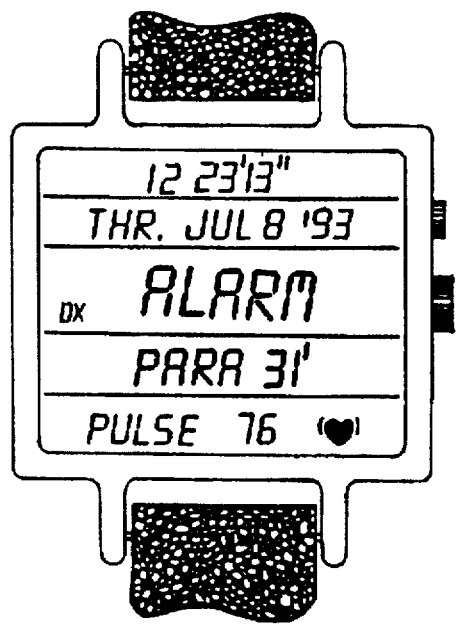

FIG. 23 illustrates a user's ALARM in the digital format based on the fourth, [4] stress formula, discussed elsewhere, and is based on an over active parasympathetic DX. This information is displayed on the fourth line of the digital format screen along with the type of over activity, which in this example is parasympathetic, and the duration of the over activity, which in this example is 31 minutes.

Figure 24:
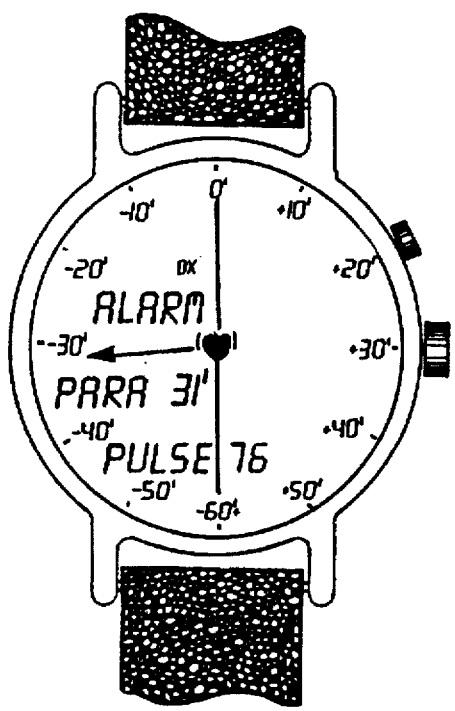

FIG. 24 illustrates a user's ALARM on the stress/distress screen of the round analog/digital standard watch based format on the fourth, [4] stress formula, discussed elsewhere, and is based on an over active parasympathetic DX. This information is displayed in the left hemisphere of the analog/digital format screen. The type of over activity, which in this example is parasympathetic, and the duration of the over activity, which in this example is 31 minutes.

Figure 25:
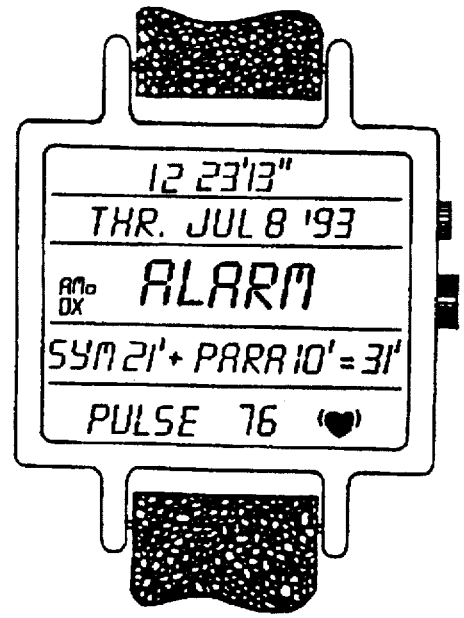

FIG. 25 illustrates a user's ALARM in the digital format based on the sixth, [6], stress formula, discussed elsewhere, and is based on an over active sympathetic and parasympathetic AMo and DX. This information is displayed on the fourth line of the digital format screen along with the type of over activity, which in this example is both sympathetic and parasympathetic, and the duration of the over activity, which in this example is 21 minutes of sympathetic and 10 minutes of parasympathetic over activity.

Figure 26:
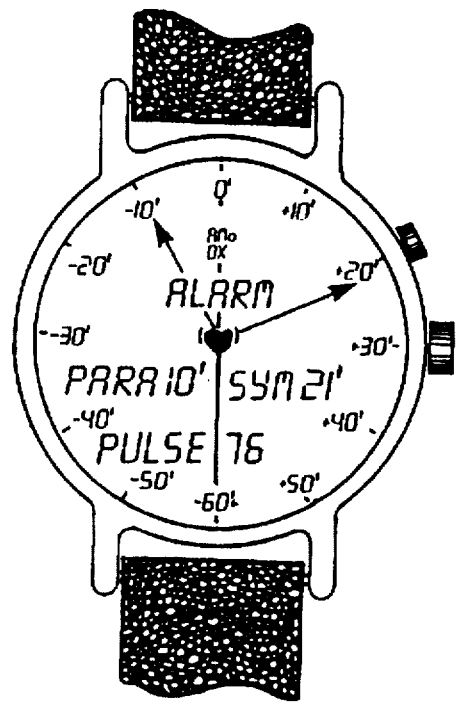

FIG. 26 illustrates a user's ALARM on the stress/distress screen of the round analog/digital standard watch based format on the sixth, [6], stress formula, discussed elsewhere, and is based on an over active sympathetic and parasympathetic AMo and DX. This information is displayed in the center of the two hemispheres of the analog/digital format screen. The type of over activity, which in this example is both sympathetic and parasympathetic, and the duration of the over activity, which in this example is 21 minutes of sympathetic and 10 minutes of parasympathetic over activity.

Figure 27:
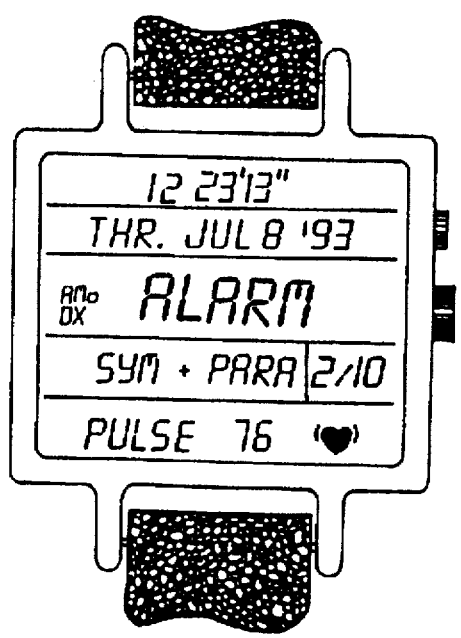

FIG. 27 illustrates a user's ALARM in the digital format based on the seventh, [7], stress formula, discussed elsewhere, and is based on an over active sympathetic and parasympathetic AMo and DX within a single Time Segment. This information is displayed on the fourth line of the digital format screen along with the type of over activity, which in this example is both sympathetic and parasympathetic, and the duration of the over activity, which in this example is two out of the previous ten Time Segments.

Figure 28:

FIG. 28 illustrates a user's ALARM of the stress/distress screen on the round analog/digital standard watch based format on the seventh, [7], stress formula, discussed elsewhere, and is based on an over active sympathetic and parasympathetic AMo and DX within a single Time Segment. This information is displayed in the center of the two hemispheres of the analog/digital format screen. The type of over activity, which in this example is both sympathetic and parasympathetic, and the duration of the over activity, which in this example is two out of the previous ten Time Segments.

Figure 29:
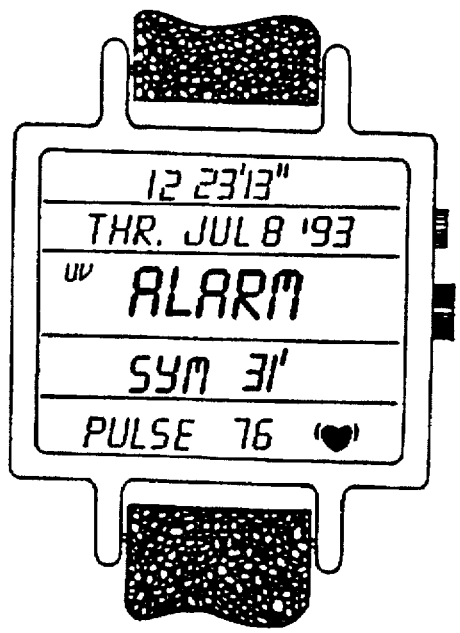

FIG. 29 illustrates a user's ALARM in the digital format based on the eighth, [8] stress formula, discussed elsewhere, and is based on an over active sympathetic UV. This information is displayed on the fourth line of the digital format screen along with the type of over activity, which in this example is sympathetic, and the duration of the over activity, which in this example is 31 minutes.

Figure 30:
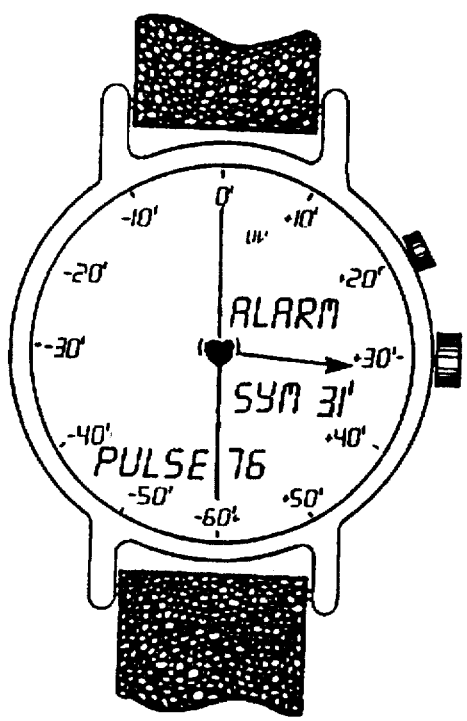

FIG. 30 illustrates a user's ALARM on the stress/distress screen of the round analog/digital standard watch based format on the eighth, [8] stress formula, discussed elsewhere, and is based on an over active sympathetic UV. This information is displayed in the right hemisphere of the analog/digital format screen. The type of over activity, which in this example is sympathetic, and the duration of the over activity, which in this example is 31 minutes.

Figure 31:
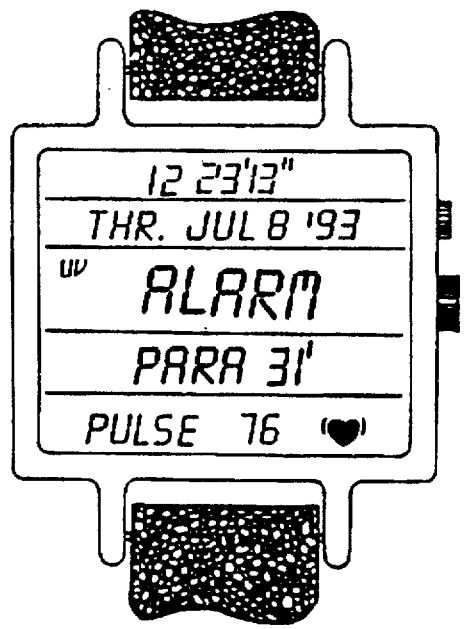

FIG. 31 illustrates a user's ALARM in the digital format based on the ninth, [9] stress formula, discussed elsewhere, and is based on an over active parasympathetic UV. This information is displayed on the fourth line of the digital format screen along with the type of over activity, which in this example is parasympathetic, and the duration of the over activity, which in this example is 31 minutes.

Figure 32:
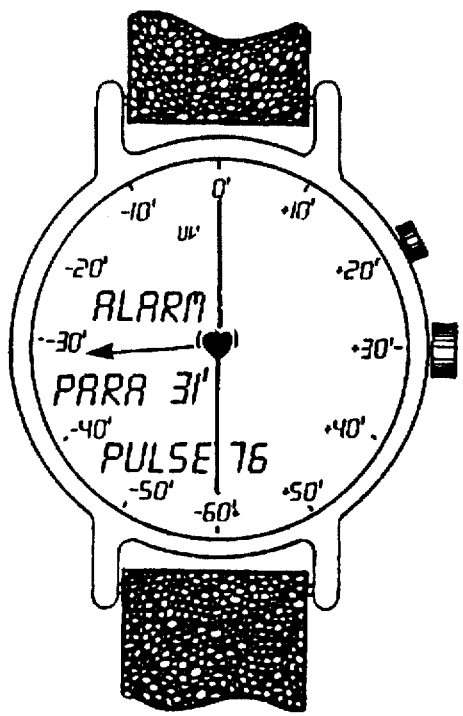

FIG. 32 illustrates a user's ALARM on the stress/distress screen of the round analog/digital standard watch based format on the ninth, [9] stress formula, discussed elsewhere, and is based on an over active parasympathetic UV. This information is displayed in the left hemisphere of the analog/digital format screen. The type of over activity, which in this example is parasympathetic, and the duration of the over activity, which in this example is 31 minutes.

Figure 33:
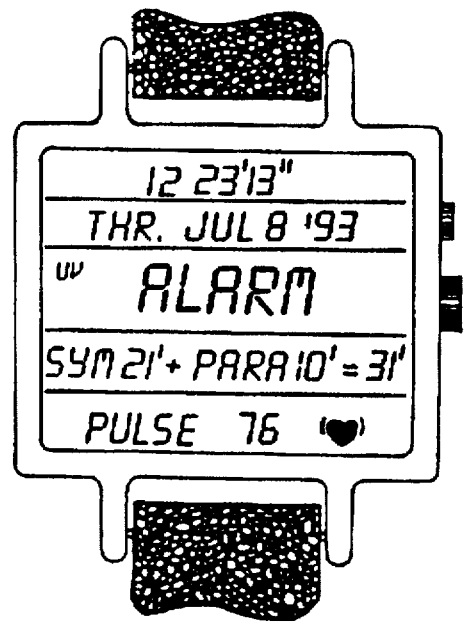

FIG. 33 illustrates a user's ALARM in the digital format based on the tenth, [10], stress formula, discussed elsewhere, and is based on an over active sympathetic and parasympathetic UV. This information is displayed on the fourth line of the digital format screen along with the type of over activity, which in this example is both sympathetic and parasympathetic, and the duration of the over activity, which in this example is 21 minutes of sympathetic and 10 minutes of parasympathetic over activity.

Figure 34:
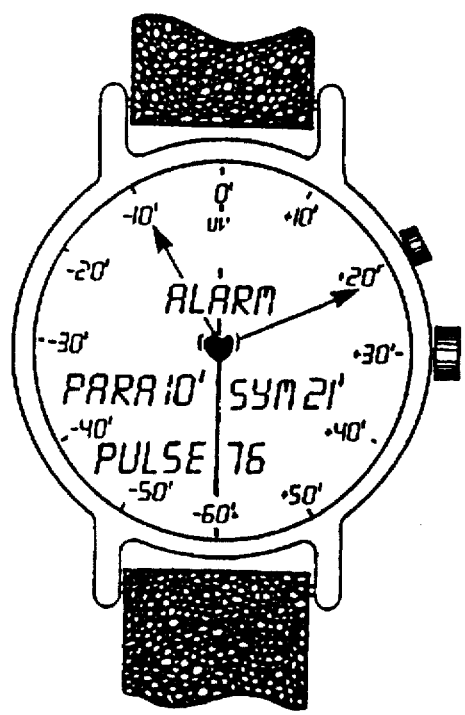

FIG. 34 illustrates a user's ALARM on the stress/distress screen of the round analog/digital standard watch based format on the tenth, [10], stress formula, discussed elsewhere, and is based on an over active sympathetic and parasympathetic UV. This information is displayed in the center of the two hemispheres of the analog/digital format screen. The type of over activity, which in this example is both sympathetic and parasympathetic, and the duration of the over activity, which in this example is 21 minutes of sympathetic and 10 minutes of parasympathetic over activity.

Figure 35:
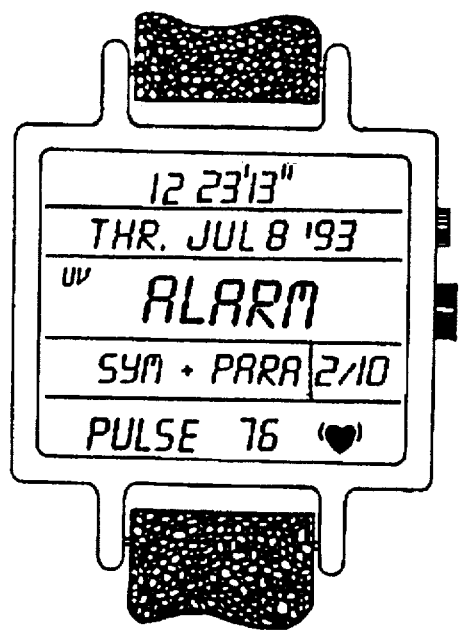

FIG. 35 illustrates a user's ALARM in the digital format based on the eleventh, [11], stress formula, discussed elsewhere, and is based-on an over active sympathetic and parasympathetic UV within a single Time Segment. This information is displayed on the fourth line of the digital format screen along with the type of over activity, which in this example is both sympathetic and parasympathetic, and the duration of the over activity, which in this example is two out of the previous ten Time Segments.

Figure 36:

FIG. 36 illustrates a user's ALARM of the stress/distress screen on the round analog/digital standard watch based format on the eleventh, [11], stress formula, discussed elsewhere, and is based on an over active sympathetic and parasympathetic UV within a single Time Segment. This information is displayed in the center of the two hemispheres of the analog/digital format screen. The type of over activity, which in this example is both sympathetic and parasympathetic, and the duration of the over activity, which in this example is two out of the previous ten Time Segments.

Figure 37:
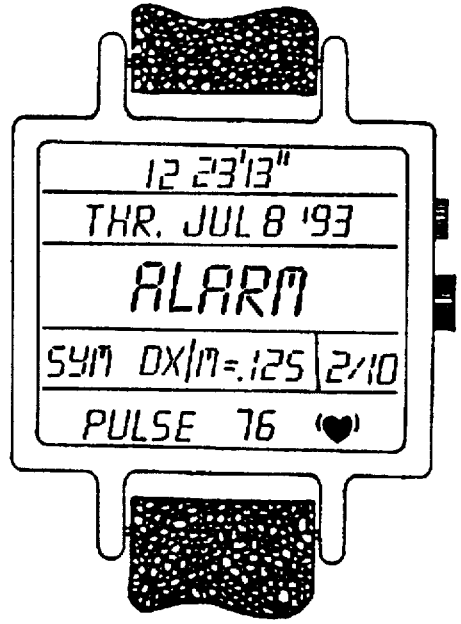

FIG. 37 illustrates a user's ALARM in the digital format based on the twelfth [12] stress formula, discussed elsewhere, and is based on an over active sympathetic system. This information is displayed on the fourth line of the digital format screen along with the type of over activity, which in this example is sympathetic, and the duration of the over activity, which in this example is two out of the previous ten Time Segments.

Figure 38:
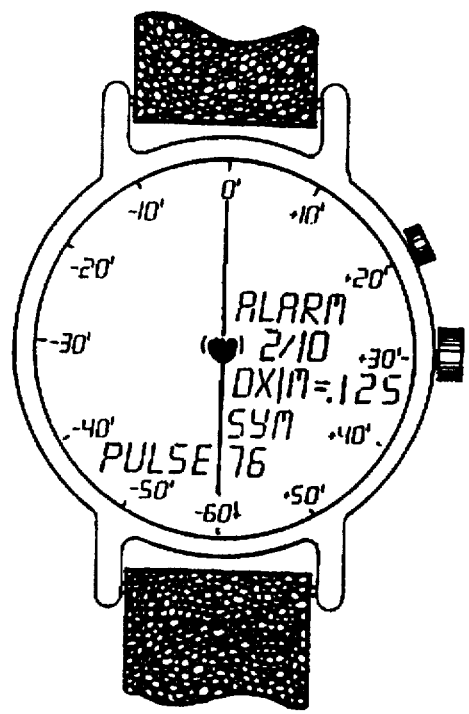

FIG. 38 illustrates a user's ALARM on the stress/distress screen of the round analog/digital standard watch based format on the twelfth, [12], stress formula, discussed elsewhere, and is based on an over active sympathetic system. This information is displayed in the right hemisphere of the analog/digital format screen. The type of over activity, which in this example is sympathetic, and the duration of the over activity, which in this example is two out of the previous ten Time Segments.

Figure 39:
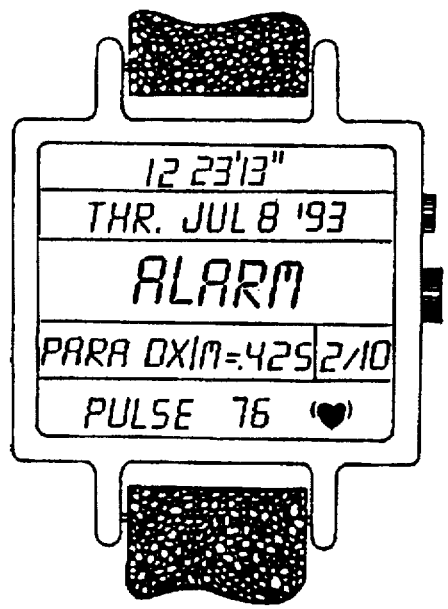

FIG. 39 illustrates a user's ALARM in the digital format based on the thirteenth [13] stress formula, discussed elsewhere, and is based on an over active parasympathetic system. This information is displayed on the fourth line of the digital format screen along with the type of over activity, which in this example is parasympathetic, and the duration of the over activity, which in this example is two out of the previous ten Time Segments.

Figure 40:
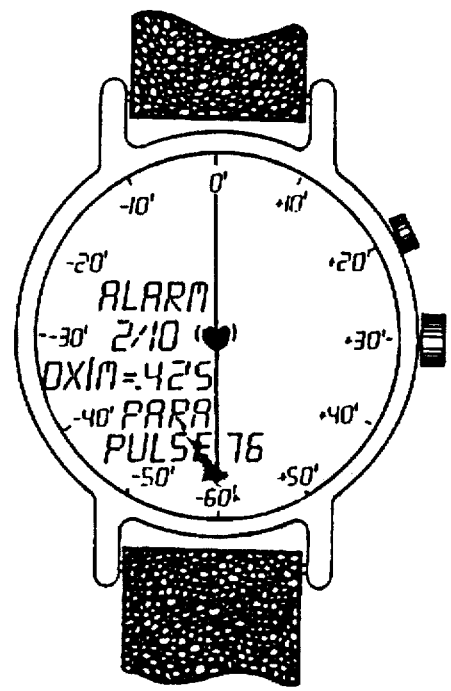

FIG. 40 illustrates a user's ALARM on the stress/distress screen of the round analog/digital standard watch based format on the thirteenth, [13], stress formula, discussed elsewhere, and is based on an over active parasympathetic system. This information is displayed in the left hemisphere of the analog/digital format screen. The type of over activity, which in this example is parasympathetic, and the duration of the over activity, which in this example is two out of the previous ten Time Segments.

Figure 41:
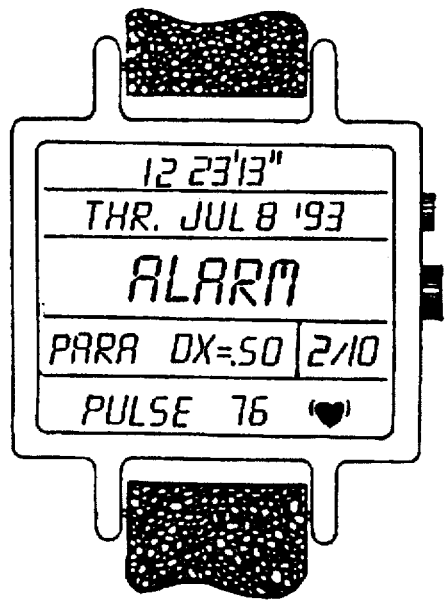

FIG. 41 illustrates a user's ALARM in the digital format based on the fourteenth, [14], stress formula, discussed elsewhere, and is based on an over active parasympathetic system. This information is displayed on the fourth line of the digital format screen, along with the type of over activity, which in this example is parasympathetic, and the duration of the over activity, which in this example is two out of the previous ten Time Segments.

Figure 42:
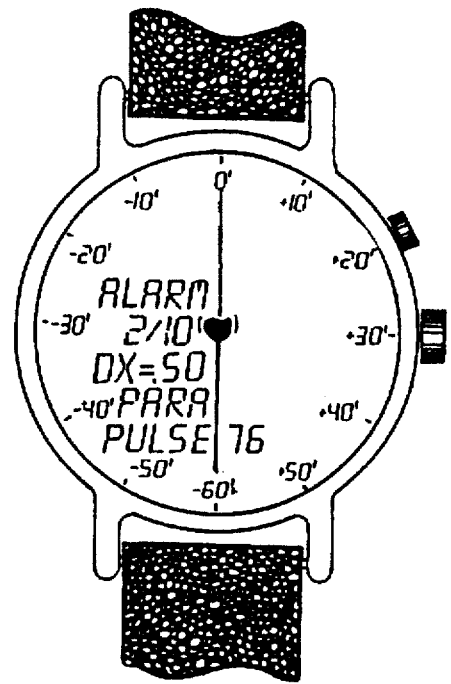

FIG. 42 illustrates a user's ALARM on the stress/distress screen of the round analog/digital standard watch based format on the fourteenth, [14], stress formula, discussed elsewhere, and is based on an over active parasympathetic system. This information is displayed in the left hemisphere of the analog/digital format screen. The type of over activity, which in this example is parasympathetic, and the duration of the over activity, which in this example is two out of the previous ten Time Segments.

Figure 43:
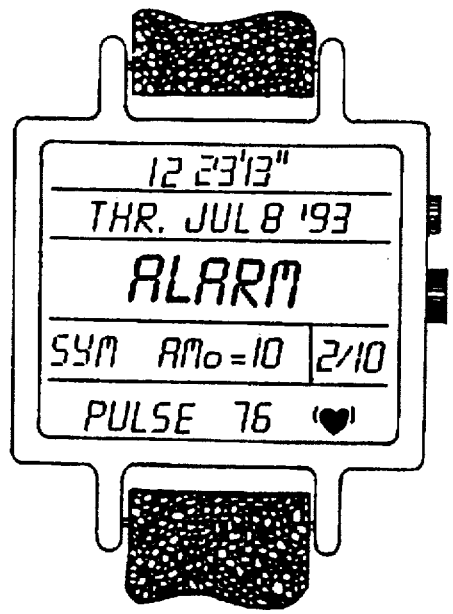

FIG. 43 illustrates a user's ALARM in the digital format based on the fifteenth, [15], stress formula, discussed elsewhere, and is based on an over active sympathetic system. This information is displayed on the fourth line of the digital format screen along with the type of over activity, which in this example is sympathetic, and the duration of the over activity, which in this example is two out of the previous ten Time Segments.

Figure 44:
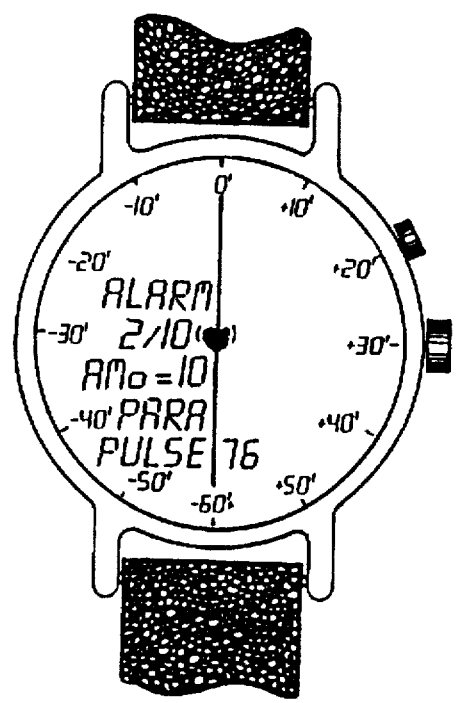

FIG. 44 illustrates a user's ALARM on the stress/distress screen of the round analog/digital standard watch based format on the fifteenth, [15], stress formula, discussed elsewhere, and is based on an over active sympathetic system. This information is displayed in the left hemisphere of the analog/digital format screen. The type of over activity, which in this example is sympathetic, and the duration of the over activity, which in this example is two out of the previous ten Time Segments.

Figure 45:
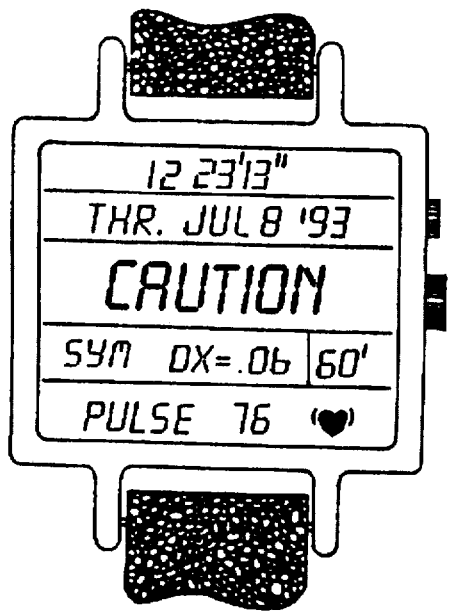

FIG. 45 illustrates a user's Caution in the digital format based on the sixteenth [16] stress formula, discussed elsewhere, and is based on an over active sympathetic system. This information is displayed on the fourth line of the digital format screen along with the type of over activity, which in this example is sympathetic, and the duration of the over activity, which in this example is 60 minutes.

Figure 46:
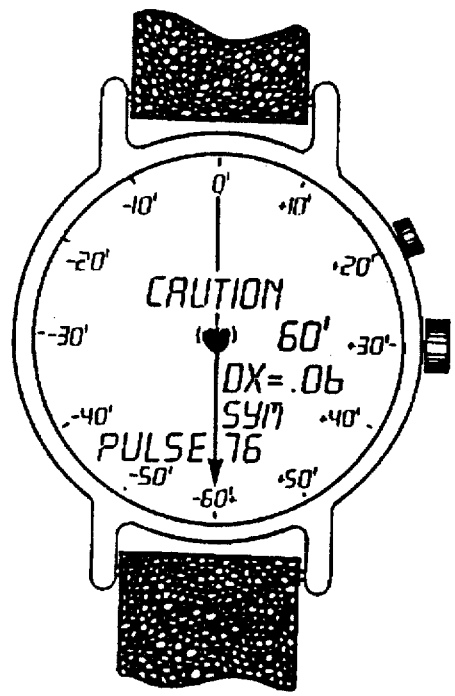

FIG. 46 illustrates a user's Caution on the stress/distress screen of the round analog/digital standard watch based format on the sixteenth, [16], stress formula, discussed elsewhere, and is based on an over active sympathetic system. This information is displayed in the right hemisphere of the analog/digital format screen. The type of over activity, which in this example is sympathetic, and the duration of the over activity, which in this example is 60 minutes.

Figure 47:
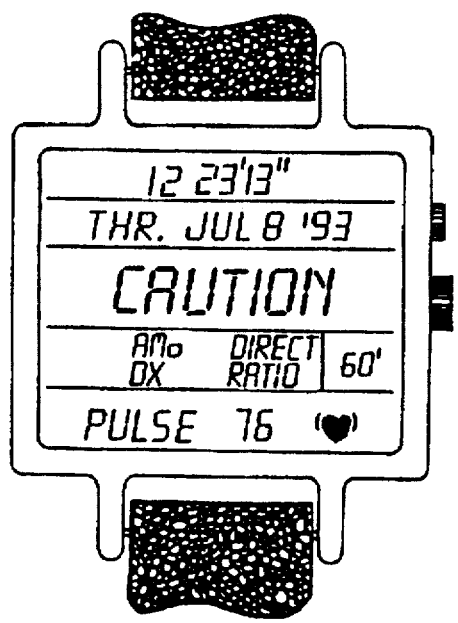

FIG. 47 illustrates a user's Caution in the digital format based on the seventeenth, [17], stress formula, discussed elsewhere, and is based on the direct ratio of AMo and DX to each other. This information is displayed on the fourth line of the digital format screen along with the type of activity, which in this example is the direct ratio of AMo and DX to each other, and the duration of the over activity, which in this example is 60 minutes.

FIG. 48 illustrates a user's Caution on the stress/distress screen of the round analog/digital standard watch based format on the seventeenth, [17], stress formula, discussed elsewhere, and is based on the direct ratio of AMo and DX to each other. This information is displayed in the center of the two hemispheres of the analog/digital format screen. The type of activity, which in this example is the direct ratio of AMo and DX to each other, and the duration of the activity, which in this example is 60 minutes.

If more than one Caution or ALARM is detected, then each such state is displayed in the appropriate location on the watch face starting with the condition generated by the first, [1], formula and ending with the seventeenth, [17], formula. Each such Caution or ALARM is displayed for five seconds.

Figure 49:
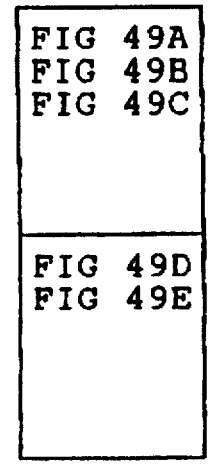
FIG. 49 is a diagram showing how FIGS. 49A, 49B, 49C, 49D and 49E may be placed together to form FIG. 49, which is a flow chart showing the processing of a preselected number of heart beat Time Intervals to determine the user's OK Zone, the Sympathetic ALARM Zone, the Parasympathetic ALARM Zone, and the multiplier factors, which determine an ALARM according to the invention.

FIG. 49A represents the minimum number, (3), of daytime Modes needed to create a user's recorded Cluster Mode, which begins with the shortest recorded Mode, (Mo 1), and progresses to the next shortest, (Mo 2) and the next shortest (Mo 3). These Modes are 0.02 seconds longer than the previous Mode. The respective recorded user values for UV, AMo, and DX for each Mode are shown. An attempt should be made to record two hours of the user's nighttime Modes. This should produce a matrix that looks like FIG. 49B.

FIG. 49B illustrates two user recorded Cluster Modes and the user values for UV, AMo, and DX. For data to be valid in the 2nd Cluster Mode, it must contain three or more entries. If this approach fails, then there is a need to infer the values for UV, AMo, and DX using ratio and proportion. Thus, [UV2:UV3::UV3::UV4], and [UV3:UV4::UV4:UV5], etc., etc. Also values should be inferred for UV, A/do, and DX for shorter Modes so that there is a minimum of three Cluster Modes as shown in FIG. 49C.

In FIG. 49C The three values for UV, Amo, and DX in each Cluster Mode are averaged, which establishes the user's baseline UV, AMo, and DX in each Cluster Mode.

In FIG. 49D the ALARM multiplier factors are inserted to establish the sympathetic and parasympathetic ALARM Zones, and thus the OK Zone between the two ALARM Zones.

If the Mode of a 101 Time Interval Time Segment falls within the 1st Cluster Mode of X to X+0.04, then the ALARM levels designated for this Cluster Mode are used. If a Mode is sensed that is not within one of the three minimum Cluster Modes, then the ALARM levels in the Cluster Mode whose values are closest to user's current values are used.

In FIG. 50, the patient's heart rhythm is variable. This is evidenced by DX=0.16 and AMo=27, which is characteristic of a natural autonomic balance between the sympathetic and the parasympathetic nervous system.

In FIG. 51, the patient's heart rhythm is not variable. This is evidenced by DX=0.04 and AMo=52, which is characteristic of an over active sympathetic nervous system.

Figure 52:
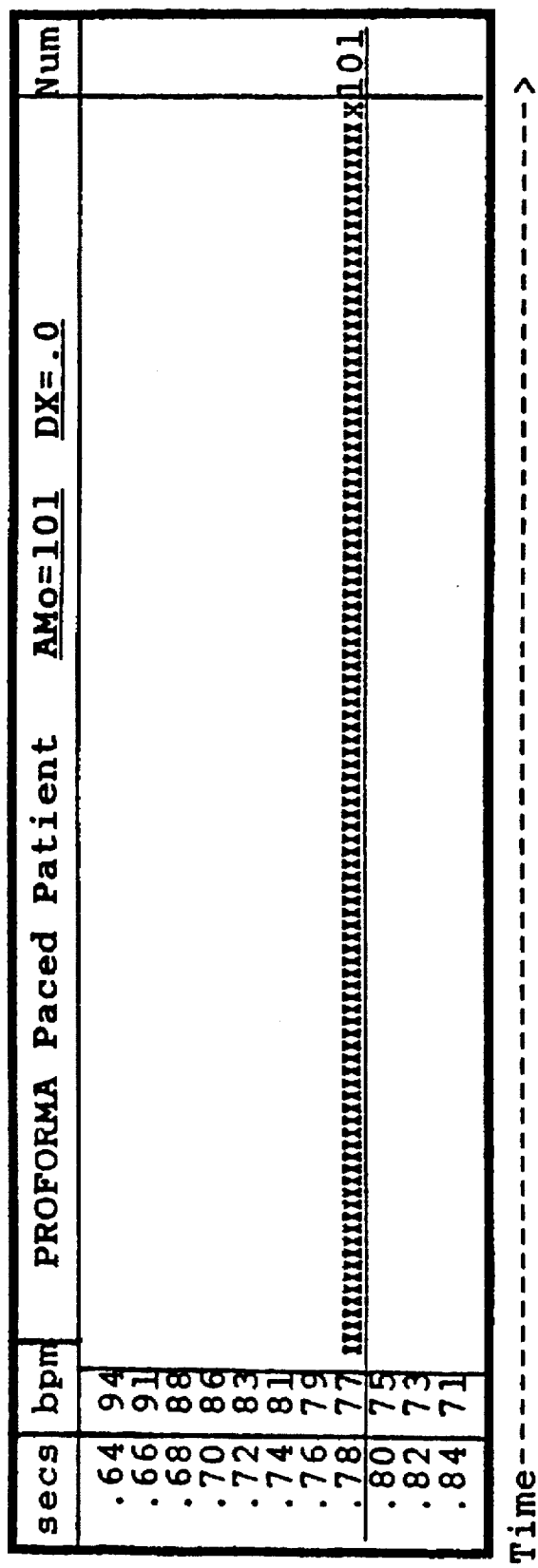
FIG. 52 is a diagram showing how patients are presently paced with ordinary pacemakers at a constant heart rate.

In FIG. 52 the patient's heart paced by a pacemaker or a cardioverter defibrillator with a pacemaker has no heart rhythm variability. This is evidenced by DX=0 and AMo= 101, which is characteristic of an extremely over active sympathetic nervous system.

FIG. 53 At birth and through youth, the heart's OK Zone regarding variability is wide. With the onset of middle age and into old age the heart's OK Zone regarding variability narrows. A deviation in the heart's variability of more than approximately +15% indicates an over stressed sympathetic system in the Sympathetic ALARM Zone, and a deviation of more than −15% indicates an over stress parasympathetic system in the Parasympathetic ALARM Zone.

FIG. 54 The inventors suggest a user patient's life can be prolonged by first detecting the onset of an arrythmia before it occurs and then, (1) pacing the patient with his/her own naturally variable heart rhythm or (2) pacing the patient using the variable heart rhythm of a healthy individual matched to the patient's age, sex and physical condition, or (3) using a random number generator programmed to emulate the heart rhythm of a healthy individual matched to the patient's age, sex and physical condition.

Just as pacing a patient with bradycardia treats the symptom and prolongs life, so the inventors suggests that pacing a user patient with a narrow heart rhythm variability with a wider heart rhythm variability treats the symptom and will prolong the user patient's life.

FIG. 55 is a chart of Patient E2's ECG Holter monitor tape as interpreted by FIG. 4A, 4B, and 4C using formulas [8] and [9], e.g. User Value.

From hour 00 to hour 02 Patient E2's baseline is established for two Cluster Modes. Using a multiplier factor, E2's OK Zone is established between the Sympathetic ALARM Zone at 10.1, and the Parasympathetic ALARM Zone at 6.6. Thus, E2's UV OK Zone is between 10.1 and 6.6.

Starting in Hour 03 through Hour 08, Patient E2 experienced an overactive Sympathetic response after 0.30 minutes, which triggered three UV Sympathetic ALARMs [8]. Halfway through Hour 08, Patient E2's autonomic nervous system suddenly changed from an over active Sympathetic response to an over active Parasympathetic response triggering a four ALARM, a Mixed UV Sympathetic/Parasympathetic ALARM-Short Term [11]. From halfway through Hour 08 to halfway through Hour 18, when Patient E2 expired due to Sudden Cardiac Death, Patient E2's autonomic nervous system experienced an almost continuous over active parasympathetic response trigger multiple UV Parasympathetic ALARMs [9].

Halfway though Hour 08, Patient E2's OK zone between UV 10.1 and 6.6 changed to between UV 10.9 and 7.0, because E2's heart rate changed from approximately 77 beats per minute to approximately 71 beats per minute, thus changing the Cluster Mode, which determined the UV Sympathetic and Parasympathetic ALARM Zones.

Pacemaker and Cardioverter Defibrillator with a Pacemaker

As previously mentioned, if the CPU in a cardioverter defibrillator with a pacemaker or a pacemaker detects an ALARM condition in the User's Heart, as described with reference to FIG. 4A, 4B, and 4C, then, as described with reference to FIG. 11 and based on the additional data from the Respiration Detector and the Galvanic Skin Detector, the Pace Signal Generator will commence pacing the User's Heart for a predetermined period of time.

There at least two types of pacemakers today that pace a user's heart based on the user's respiration, which are incorporated in a cardioverter defibrillator or a stand alone pacemaker. These are (1) transthoracic, or (2) impedance. A transthoracic pacemaker measures the expansion and contraction of the user's chest while inhaling and exhaling. An impedance pacemaker measures the electrical resistance in the air of the user's lungs while inhaling and exhaling. When the user inhales, the heart rate increases, and when the user exhales, the heart rate decreases.

Hereafter, the term pacemaker refers both to a stand alone pacemaker and a cardioverter defibrillator with a pacemaker, unless otherwise noted.

Therefor in order to program a cardioverter defibrillator with a pacemaker or a pacemaker, the patient user's Holter monitor records ECG RR together with respiratory and galvanic skin response baseline data as follows:

Daytime at rest for at least two hours
Nighttime at rest for at least two hours
Daytime exercise for at least 30 minutes sustained exercise Then the Holter monitor ECG recordings should be edited deleting low variability episodes.

Then the ECG RR, the respiratory, and the galvanic skin response baseline data are stored in the pacemaker.

The stress formulas [1] through [17] are stored in the memory of the pacemaker.

When the pacemaker detects an ALARM, as defined in formulas [1] through [17], then the pacemaker will pace the user's heart using the user's appropriate variable heart rhythm data that occurred at the same time as the user's current respiratory state previously recorded, and, if possible the user's galvanic skin response state, all as described above for a period of 10 minutes.

Then if the user's heart rhythm still generates ALARMs after 10 minutes of non-pacing, the pacemaker will again pace the user's heart for 100 minutes, again matching the user's heart rate variability with the user's respiratory state, and, if possible, the user's galvanic skin response state.

Then if a natural, variable sinus rhythm does not resumed after 100 minutes of non pacing, then the pacemaker paces the heart for 1,000 minutes and so on in increasing powers of 10, or as programmed by the user's cardiologist.

If a cardioverter defibrillator with a pacemaker detects tachycardia, then the cardioverter defibrillator with a pacemaker will respond with a single extrastimulus burst, a double extrastimuli burst, or multiple extrastimuli bursts, as programmed.

Periodically, the user's recorded values for UV, AMo, and DX are down loaded to a PC from the user's pacemaker by telemetry for analysis of sympathetic and parasympathetic trends. All ALARM episodes, if any, as well a single extrastimulus burst, a double extrastimuli burst, or multiple extrastimuli bursts, in a cardioverter defibrillator with a pacemaker, if any, are date and time stamped.

If a Holter tape of the user's normal, variable heart rate is not available, then preferably the user is paced with a recording from a subject matched by age, race, sex, and physical condition, and also matched to the user's respiratory rates, and, if possible, to the user's galvanic skin response.

However, the user may be paced at a generated, histographically normal variable rate, matched to the user's respiratory rates, and the generated heart rate varied by the transthoracic or impedance pacemaker matching the user's respiratory rate simulating the wide saw tooth variability patterns of Time Intervals occurring naturally with reference to FIG. 50, and, if possible, to the user's galvanic skin response.

It will thus be seen that the objects set forth above, among those made apparent from the preceding descriptions: are efficiently attained and, since certain changes may be made in carrying out the above method in the apparatus set forth, without departing from the scope of the invention, it is intended that all matter contained in the above description or shown in the accompanying drawings and charts shall be interpreted as illustrative and not limiting in sense.

Having described our invention, what we claim as new and desire to secure by Letters Patent is:

1. A method of detecting abnormal heart rate variability comprising:

A) first recording a first subject's RR or SOS intervals over substantially no less than 50 to substantially no more than 300 heart beat segments occurring with normal heart rate variability;

B) characterizing the sharpness of histograms of said segments comprising the numbers of each of the RR intervals recorded versus each particular RR interval as a function of the Mode of each of said segments;

C) second recording a second subject's RR or SOS intervals over substantially no less than 50 to substantially no more than 300 heart beat segments;

D) characterizing the sharpness of the histograms of said second subject's RR interval variations as a function of the Mode of each of said segments; and E) indicating when the sharpness of the histograms of said second subject deviates from predetermined limits derived from the histograms of said first subject.

2. The method defined in claim 1 wherein said sharpness is characterized by the Amplitude of the Mode (AMo) occurring in said segments.

3. The method defined in claim 2 wherein said sharpness is also characterized by a number proportional to the ratio of the Amplitude of the mode (AMo) expressed as a percentage to the difference between substantially the largest and substantially the smallest RR interval in a segment (ΔX).

4. The method defined in claim 3 wherein said number (UV) is defined by an equation as follows:

$$UV = \sqrt{(0.5/X)^2 + (AMo/10)^2}$$

wherein AMo is defined as Amplitude of the mode and the segment is stated as DX.

5. The method defined in claim 3 wherein said number (UV) is defined by an equation as follows:

$$UV = \sqrt{(0.5/DX)^2 + (AM/10)^2}$$

wherein AM is defined as Amplitude of the mean and the segment is stated as DX.

6. The method defined in claim 1 wherein said sharpness is characterized by a number proportional to the ratio of the Amplitude of the mode (AMo) to the difference between substantially the largest and substantially the smallest RR interval in a segment (ΔX).

7. The method defined in claim 4 wherein said sharpness is characterized by a number proportional to the ratio of the Amplitude of the mode (AMo) expressed as a percentage to the difference between substantially the largest and substantially the smallest RR interval in a segment (ΔX).

8. The method defined in claim 1 wherein said first recording is made when said first subject is in normal autonomic balance.

9. The method defined in claim 8 wherein said first and second recordings are made when said first and second subjects are performing a function chosen from the group consisting of sleep, awake resting, awake exercising, and awake recovering from exercising.

10. The method defined in claim 1 and further comprising the step of:

F) applying pacemaker stimulus to the heart of said second subject upon the occurrence of said indication.

11. The method defined in claim 1 and further comprising the step of:

F) applying electrocardioverting defibrillating stimulus to the heart of said second subject upon the occurrence of said indication.

12. Apparatus adapted to perform the method defined in claim 1, comprising

A) means for first recording a first subject's RR or SOS intervals over substantially no less than 50 to substantially no more than 300 heart beat segments occurring with normal heart rate variability;

B) means for characterizing the sharpness of histograms of said segments comprising the numbers of each of the RR or SOS intervals recorded versus each particular RR interval as a function of the Mode of each of said segments;

C) means for second recording a second subject's RR or SOS intervals over substantially no less than 50 to substantially no more than 300 heart beat segments;

D) means for characterizing the sharpness of the histograms of said second subject's RR or SOS interval variations as a function of the Mode of each of said segments; and E) means for indicating the sharpness of the histograms of said second subject deviates from predetermined limits derived from the histograms of said first subject.

13. Apparatus as defined in claim 12 further defined as comprising:

A) a module adapted to be strapped to the wrist comprising,
   a) a passive RR interval detector, and
   b) radio means for conveying said indication to a telephonic communications device.

14. Apparatus as defined in claim 13 wherein said telephonic communications device is a cellular telephone.

15. Apparatus as defined in claim 14 wherein said passive RR interval detector detects the second subject's pulse.

16. Apparatus as defined in claim 13 wherein said module further comprises:
   c) a motion detector, and
   d) means responsive to said motion detector to distinguish between the states of wakefulness, sleep, and coma.

17. The apparatus of claim 12, wherein the means for recording the second subject's RR intervals records the intervals as non-invasive ECG RR signals or pulse signals.

18. The method defined in claim 1 wherein said sharpness is characterized by the Amplitude of the Mean (AM) occurring in said segments.

19. The method defined in claim 18 wherein said sharpness is also characterized by a number proportional to the ratio of the Amplitude of the Mean (AM) expressed as a percentage to the difference between substantially the largest and substantially the smallest RR interval in a segment (ΔX).

20. An apparatus for performing the method defined in claim 18 for detecting abnormal heart rate variability comprising:

A) means for first recording a first subject's RR intervals over substantially no less than 50 to substantially no more than 300 heart beat segments occurring with normal heart rate variability;

B) means for characterizing the sharpness of histograms of said segments comprising the numbers of each of the RR intervals recorded versus each particular RR interval as a function of the Mode of each of said segments;

C) means for second recording a second subject's RR intervals over substantially no less than 50 to substantially no more than 300 heart beat segments:

D) means for characterizing the sharpness of the histograms of said second subject's RR interval variations as a function of the Mode of each of said segments; and E) means for indicating when the sharpness of the histograms of said second subject deviates from predetermined limits derived from the histograms of said first subject, wherein said sharpness is characterized by the Amplitude of the Mean (AM) occurring in said segments.

21. The method defined in claim 1 wherein said sharpness is characterized by a number proportional to the ratio of the Amplitude of the Mean (AM) to the difference between substantially the largest and substantially the smallest RR interval in a segment (X).

22. The method defined in claim 1 wherein said sharpness is characterized by a number proportional to the ratio of the Amplitude of the Mean (AM) expressed as a percentage to the difference between substantially the largest and substantially the smallest RR interval in a segment ($\Delta X$).

23. The method defined in claim 1, wherein said sharpness is characterized by a number proportional to the ratio of the Amplitude of the mode (AMo) to the difference between substantially the largest and substantially the smallest RR interval in a segment of width at half maximum of said histogram.

24. The method defined in claim 1, wherein said sharpness is characterized by a number proportional to the ratio of the Amplitude of the mode (AMo) expressed as a percentage to the difference between substantially the largest and substantially the smallest instantaneous heart rate or RR interval in a segment of standard deviation of said histogram.

25. The method defined in claim 1, wherein said sharpness is characterized by the Amplitude of the Median occurring in said segments.

26. The method of claim 1, wherein the second subject's intervals are recorded as non-invasive ECG RR signals or pulse signals.

27. The method of operating a heart rate pacemaker regulating a patient subject's heart comprising varying the rate of said pacemaker to induce heart rate variability to the patient subject at a desired heart rate mode.

28. The method defined in claim 27 wherein said method comprises the steps of:
  A) recording a heart rate for a predetermined interval when said rate is occurring normally; and
  B) using said recording to generate pacemaker signals applied to the patient subject to pace the patient subject's heart rate in accordance with said recording.

29. The method defined in claim 28 wherein said recording is of the patient subject's own heart rate.

30. The method of claim 27 wherein said recording is of substantially at least fifty heart beats.

31. The method of claim 27 wherein said recording is of substantially at least 100 heart beats.

32. The method of claim 27 wherein said recording is of substantially no more than 1,000 heart beats.

33. The method of claim 27 wherein said recording is of substantially no more than 300 heart beats.

34. The method defined in claim 28 wherein several said recordings are made corresponding to differing heart rate modes and each is used when the corresponding differing heart rate mode is desired.

35. The method defined in claim 27 comprising applying a series of pacemaker signals to the patient subject to provide a histographic profile of RR interval occurrences corresponding to said normal random heart rate variability of said patient subject.

36. The method defined in claim 35 wherein said histographic profile varies with the required heart rate mode.

37. The method defined in claim 27 wherein said normal random heart rate variability varies in character at differing heart rate modes.

38. The method defined in claim 27 and measuring the patient subject's breathing state and further varying the rate of said pacemaker to correspond to the variability of the patient subject's heart rate when in said breathing state.

39. The method defined in claim 38 and measuring one or more other of the patient subject's stress state indicators and further varying the state of said pacemaker to correspond to the variability of the patient subject's heart rate when said measured stress state.

40. The method defined in claim 27 wherein said varying rate is a random distribution producing a normal histogram.

41. An apparatus for performing the method defined in claim 27 comprising means for operating a heart rate pacemaker regulating a patient subject's heart comprising, means for varying the rate of said pacemaker to correspond to random heart rate variability of the patient subject at a desired heart rate mode.

42. The method of claim 27, further comprising detecting onset of an arrythmia before the arrythmia occurs, wherein the pacemaker rate is varied in response to said detecting.

43. A method for detecting abnormal heart rate variability comprising:
  A) first recording a subject's heart beat intervals instantaneous heart rates over substantially no less than 50 to substantially no more than 300 heart beat intervals;
  B) characterizing the histogram of said recorded intervals rates comprising the number of occurrences of each of the intervals or rates recorded versus each particular interval or rate to determine at least one characteristic of heart rate variability selected from the group consisting of a characteristic of sympathetic activity and a characteristic of parasympathetic activity;
  C) measuring for onset of an arrythmia before the arrhythmia occurs by comparing said at least one characteristic of said histogram with at least one predetermined limit to determine if said at least one characteristic exceeds said at least one predetermined limit.

44. The method of claim 43, wherein said characteristic may be any member of the group consisting of UV, AMo, and DX.

45. The method defined in claim 44 wherein at least one of said limits is time dependent.

46. The method defined in claim 45 wherein at least one of said limits is exceeded by three or more successive recordings of substantially no less than 50 to substantially no more than 300 heart beats.

47. The method defined in claim 46 wherein said indicating step occurs when a current AMo limit is exceeded by approximately +70% or −70% of a baseline value for AMo in each recorded heart rate Mode thus indicating imbalance of the subject's autonomic system.

48. The method defined in claim 46 wherein said indicating step occurs when a current DX limit is exceeded by approximately +70% or −70% of a baseline value for DX in each recorded heart rate Mode thus indicating imbalance of the subject's autonomic system.

49. The method defined in claim 46 wherein said indicating step occurs when a current UV limit is exceeded by approximately +70% or −70% of a baseline value for UV in each recorded heart rate Mode thus indicating imbalance of the subject's autonomic system.

50. An apparatus for performing the method defined in claim 43 for detecting abnormal heart rate variability comprising:
  A) means for recording a subject's heart beat intervals over substantially no less than 50 to substantially no more than 300 heart beat intervals;
  B) means for characterizing the histogram of said recorded intervals comprising the number of occurrences of each of the intervals recorded versus each particular interval to determine at least one characteristic of heart rate variability selected from the group consisting of a characteristic of sympathetic activity and a characteristic of parasympathetic activity;

C) means for measuring for onset of an arrhythmia before the arrhythmia occurs by comparing said at least one characteristic of said histogram with at least one predetermined limit to determine if said at least one characteristic exceeds said at least one predetermined limit.

51. The apparatus defined in claim 50, wherein said characteristic comprises a member of the group of UV, AMo, or DX.

52. The apparatus defined in claim 50, wherein the means for characterizing determines said characteristic of sympathetic activity.

53. The apparatus defined in claim 50, wherein the means for characterizing determines said characteristic of parasympathetic activity.

54. The apparatus of claim 14, wherein the means for recording the subject's heart beat intervals records the intervals as non-invasive ECG RR signals or pulse signals.

55. An apparatus for performing the method defined in claim 44 further comprising a module strapped to the user's wrist comprising, a) a passive SOS Time Interval sensor, and b) radio means for conveying time intervals recorded by the SOS Time Interval sensor and the characteristics of the histogram to a member selected from the group consisting of a telephonic communications device, a passive ECG heart rate sensor and an RR Time Interval sensor.

56. The apparatus as defined in claim 55, wherein said telephonic communications device is a cellular telephone comprising, a) a strobe light, and b) a voice microprocessor with CPR instructions, the capability of flashing the user's front door light, and the capability of unlocking the user's front door.

57. The apparatus as defined in claim 55, wherein said passive SOS sensor detects the time intervals of the pulse, or ECG heart rate or RR Time Interval sensor.

58. The apparatus as defined in claim 55, wherein said module further comprises:

a) a motion sensor, b) means responsive to said motion sensor to distinguish between the states of coma, sleep, wakefulness, and physical activity, c) a galvanic skin sensor, and d) means responsive to said galvanic skin sensor to distinguish between the states of connectivity, or lack of connectivity to the wrist module to the user's wrist.

59. The apparatus defined in claim 55, wherein said module further comprises:

a) a motion sensor, and b) means responsive to said motion sensor to distinguish between the states of coma, sleep, wakefulness, and physical activity.

60. The apparatus defined in claim 55, wherein said module further comprises:

a) a galvanic skin sensor, and b) means responsive to said galvanic skin sensor to distinguish between the states of connectivity, or lack of connectivity to the wrist module to the user's wrist.

61. The method defined in claim 43, further comprising indicating occurrences of said at least one characteristic exceeding said predetermined limits.

62. The method defined in claim 43, further comprising sensing motion of the subject and distinguishing between the states of the subject of coma, sleep, wakefulness and physical activity.

63. The method defined in claim 43, further comprising employing a galvanic skin sensor to sense galvanic skin data, and distinguishing between states of connectivity, or lack of connectivity of the subject's wrist to the galvanic skin sensor.

64. The method of claim 43, wherein at least one said characteristic of sympathetic activity is determined.

65. The method of claim 43, wherein at least one said characteristic of parasympathetic activity is determined.

66. The method of claim 43, wherein the subject's heart beat intervals or instantaneous heart rates are recorded as non-invasive ECG RR signals or pulse signals.

* * * * *

UNITED STATES PATENT AND TRADEMARK OFFICE
CERTIFICATE OF CORRECTION

PATENT NO. : 5,718,235

DATED : February 17, 1998

INVENTOR(S) : Boris GOLOSARSKY et al

It is certified that error appears in the above-identified patent and that said Letters Patent is hereby corrected as shown below:

Claim 1, line 8, after "RR" insert --or SOS--;
 line 9, after "RR" insert --or SOS--;
 line 15, after "RR" insert --or SOS--.

Claim 12, line 10, after "RR" insert --or SOS--.

Claim 43, line 3, after "intervals" insert --or--;
 line 6, after "intervals" insert --or--.

Signed and Sealed this

Fifteenth Day of June, 1999

Attest:

Attesting Officer

Q. TODD DICKINSON

Acting Commissioner of Patents and Trademarks